US012761224B2

(12) United States Patent
Dolloff et al.

(10) Patent No.: US 12,761,224 B2
(45) Date of Patent: Oct. 13, 2026

(54) AGR2Xcd3 BISPECIFIC ENGAGER FOR THE TREATMENT OF CANCER

(71) Applicant: MUSC FOUNDATION FOR RESEARCH DEVELOPMENT, Charleston, SC (US)

(72) Inventors: Nathan G. Dolloff, Mount Pleasant, SC (US); Reeder M. Robinson, Charleston, SC (US)

(73) Assignee: MUSC FOUNDATION FOR RESEARCH DEVELOPMENT, Charleston, SC (US)

( * ) Notice: Subject to any disclaimer, the term of this patent is extended or adjusted under 35 U.S.C. 154(b) by 617 days.

(21) Appl. No.: 18/259,640

(22) PCT Filed: Jan. 4, 2022

(86) PCT No.: PCT/US2022/070009

§ 371 (c)(1),
(2) Date: Jun. 28, 2023

(87) PCT Pub. No.: WO2022/150803

PCT Pub. Date: Jul. 14, 2022

(65) Prior Publication Data

US 2024/0085427 A1 Mar. 14, 2024

Related U.S. Application Data

(60) Provisional application No. 63/134,093, filed on Jan. 5, 2021.

(51) Int. Cl.
*G01N 33/575* (2026.01)
*A61K 39/00* (2006.01)
*C07K 16/28* (2006.01)

(52) U.S. Cl.
CPC ..... *G01N 33/57585* (2026.01); *C07K 16/283* (2013.01); *A61K 2039/505* (2013.01); *C07K 2317/31* (2013.01); *C07K 2317/622* (2013.01); *C07K 2317/94* (2013.01); *G01N 2333/99* (2013.01)

(58) Field of Classification Search
None
See application file for complete search history.

(56) References Cited

U.S. PATENT DOCUMENTS

| | | | |
|---|---|---|---|
| 8,329,875 B2 | 12/2012 | Barraclough et al. | |
| 10,669,337 B2 * | 6/2020 | Irving | A61K 39/395 |
| 2007/0231822 A1 | 10/2007 | Mitas | |
| 2017/0240651 A1 | 8/2017 | Sanofi et al. | |
| 2017/0283509 A1 | 10/2017 | Logsdson et al. | |
| 2018/0312605 A1 | 11/2018 | Kufe et al. | |
| 2019/0309060 A1 | 10/2019 | Villa et al. | |

FOREIGN PATENT DOCUMENTS

| | | | |
|---|---|---|---|
| WO | WO-2008025964 A2 * | 3/2008 | A61P 35/00 |
| WO | WO2013/040358 | 3/2013 | |
| WO | WO2015/179918 | 12/2015 | |

OTHER PUBLICATIONS

Boj, et al., Organoid models of human and mouse ductal pancreatic cancer' *Cell* 160, 324-338, doi:10.1016/j.cell.2014.12.021 (2015).
Chen, R. et al., "Elevated level of anterior gradient-2 in pancreatic juice from patietns with pre-malignant pancreatic neoplasia", *Mol Cancer* 9, 149, doi:10.1186/1476-4598-9-149 (2010).
Di Maro, et al., "Anterior gradient protein 2 promotes survival, migration and invastion of papillary thyroid carcinoma cells", *Mol Cancer* 13, 160, doi:10.1186/1476-4598-13-160 (2014).
Dumartin, et al., "AGR2 Is a Novel Surface Antigen That Promotes the Dissemination of Pancreatic Cancer Cells through Regulation of Cathepsins B and D", *Cancer Res* 71, 7091-7102, doi:10.1158/0008-5472.CAN-11-1367 (2011).
Dumartin, et al., "ER stress protein AGR2 precedues and is involved in the regulation of pancreatic cancer initiation", *Oncogene* 36, 3094-3103, doi:10.1038/onc.2016.459 (2017).
International Search Report and Written Opinion for PCT/US2022/070009 dated Jun. 3, 2022, 16 pages.
Invitation to Pay Additional Fees for PCT/US2022/070009 dated Mar. 17, 2022, 3 pages.
Le Large, et al., "Key Biological processes driving metastatis spread of pancreatic cancer as identified by multi-omics studies", *Semin Cancer Biol* 44, 153-169, doi:10.1016/j.semcancer.2017.03.008 (2017).
Ma, et al., "AGR2 promotes the proliferation, migration and regulates epithelial-mesenchymal transition in salivary adenoid cystic carcinoma", *Am J Transl Res* 9, 507-519 (2017).
Norris, et al., "AGR2 is a SMAD4-suppressible gene that modulates MUC1 levels and promotes the initiation and progression of pancreatic intraepithelial neoplasia", *Oncogene* 32, 3867-3876, doi:10.1038/onc.2012.394 (2013).
Ramachandran, et al., "Anterior gradient 2 is expressed and secreted during the development of pancreatic cancer and promotes cancer cell survival", *Cancer Res* 68, 7811-7818, doi:10.1158/0008-5472.CAN-08-1320 (2008).
Riener, et al., "Prognostic significance of AGR2 in pancreatic ductal adenocarcinoma" *Histol Histopathol* 24, 1121-1128, doi:10.14670/HH-24.1121 (2009).
Singh, et al., "SMAD4 genetic alterations predict a worse prognosis in patients with pancreatic ductal adenocarcinoma", *Pancreas* 41, 541-546, doi:10.1097/MPA.0b013e318247d6af (2012).
Wang, et al., "The Adenocarcinoma-Associated Antigen, AGR2, Promotes Tumor Growth, Cell Migration, and Cellular Transformation", *Cancer Res* 68, 492-497, doi:10.1158/0008-5472.CAN-07-2930 (2008).

(Continued)

*Primary Examiner* — Bao-Thuy L Nguyen
*Assistant Examiner* — Bonirath Chhay
(74) *Attorney, Agent, or Firm* — pH IP Law

(57) ABSTRACT

The present disclosure is directed to antibodies binding to AGR2 and cancer cells that express or overexpress AGR2, and methods for use thereof.

25 Claims, 8 Drawing Sheets

Specification includes a Sequence Listing.

(56) References Cited

OTHER PUBLICATIONS

Liu et al., "AGR2, a unique tumor-associated antigen, is a promising candidate for antibody targeting", *Oncotarget*, 10(42):4276-4289, 2019.

Negi et al., "Anterior Gradient-2 monoclonal antibody inhibits lung cancer growth and metastasis by upregulating p53 pathway and without exerting any toxicological effects: A preclinical study", *Cancer Letters*, 449:125-134, 2019.

Partial Supplementary European Search Report for EP Appl. No. 22737326.3 dated Dec. 9, 2024, 16 pages.

* cited by examiner

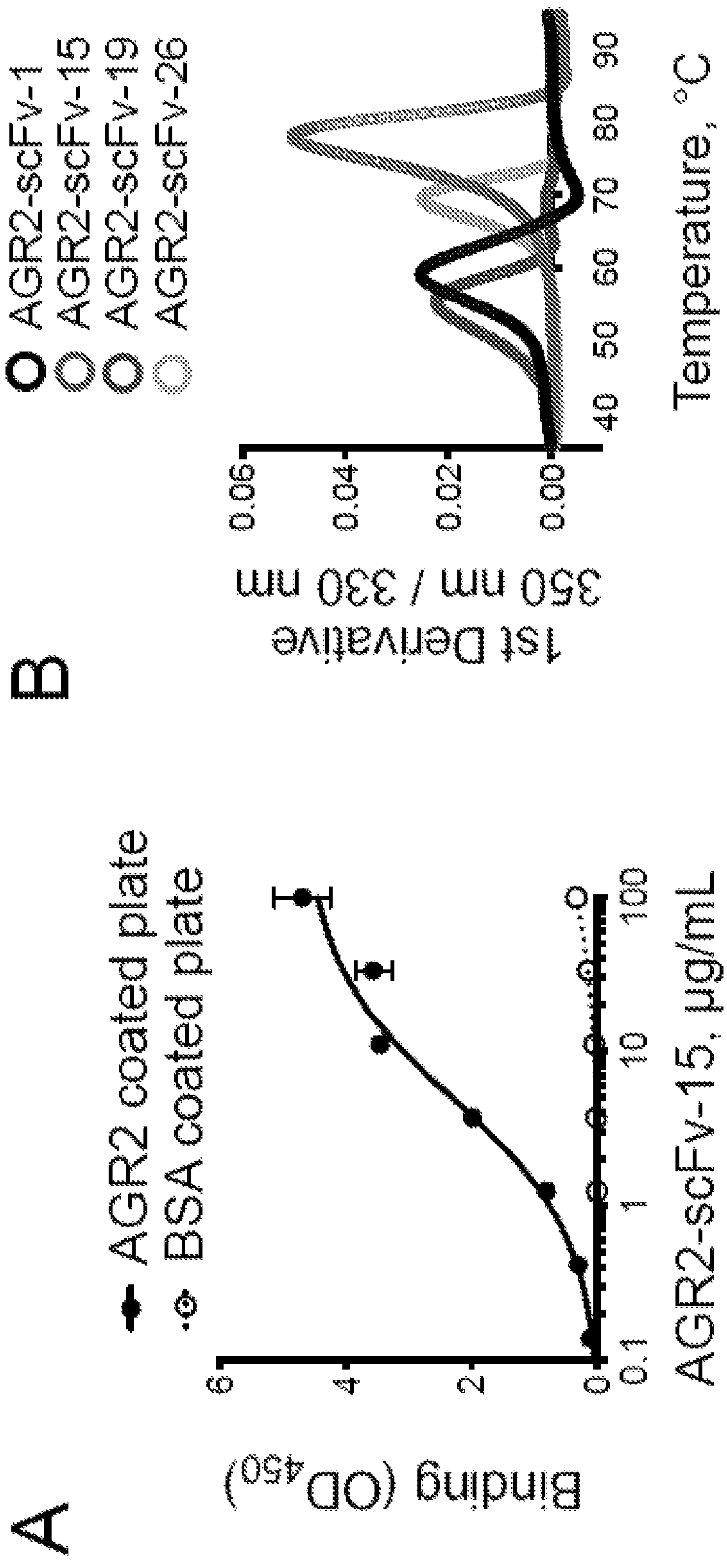
FIGS. 1A-B

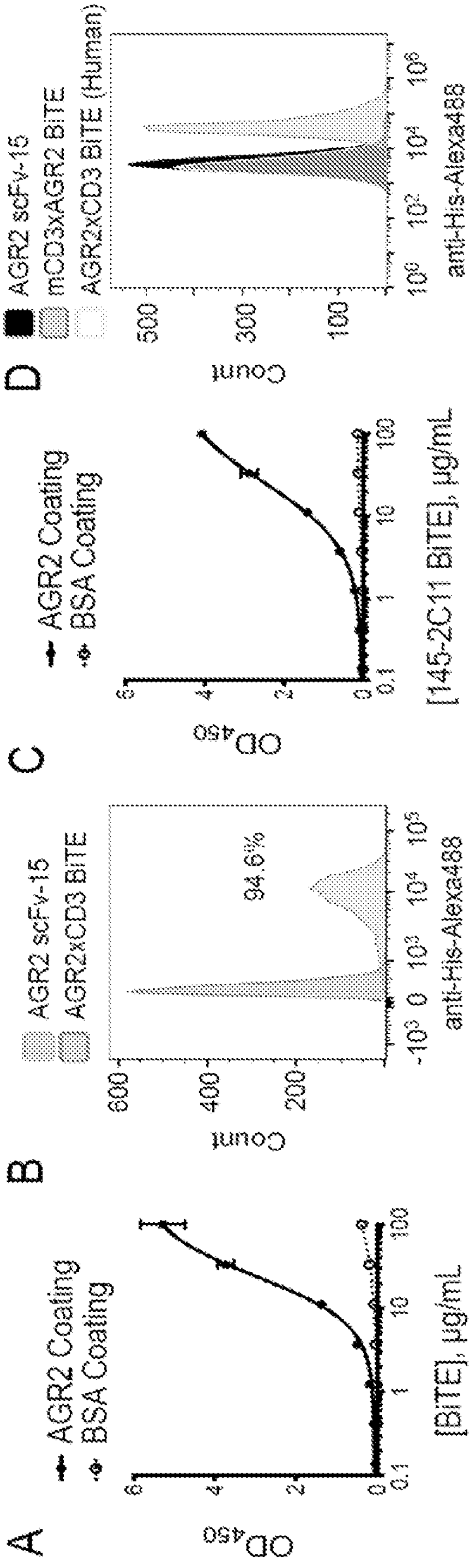
FIGS. 2A-D

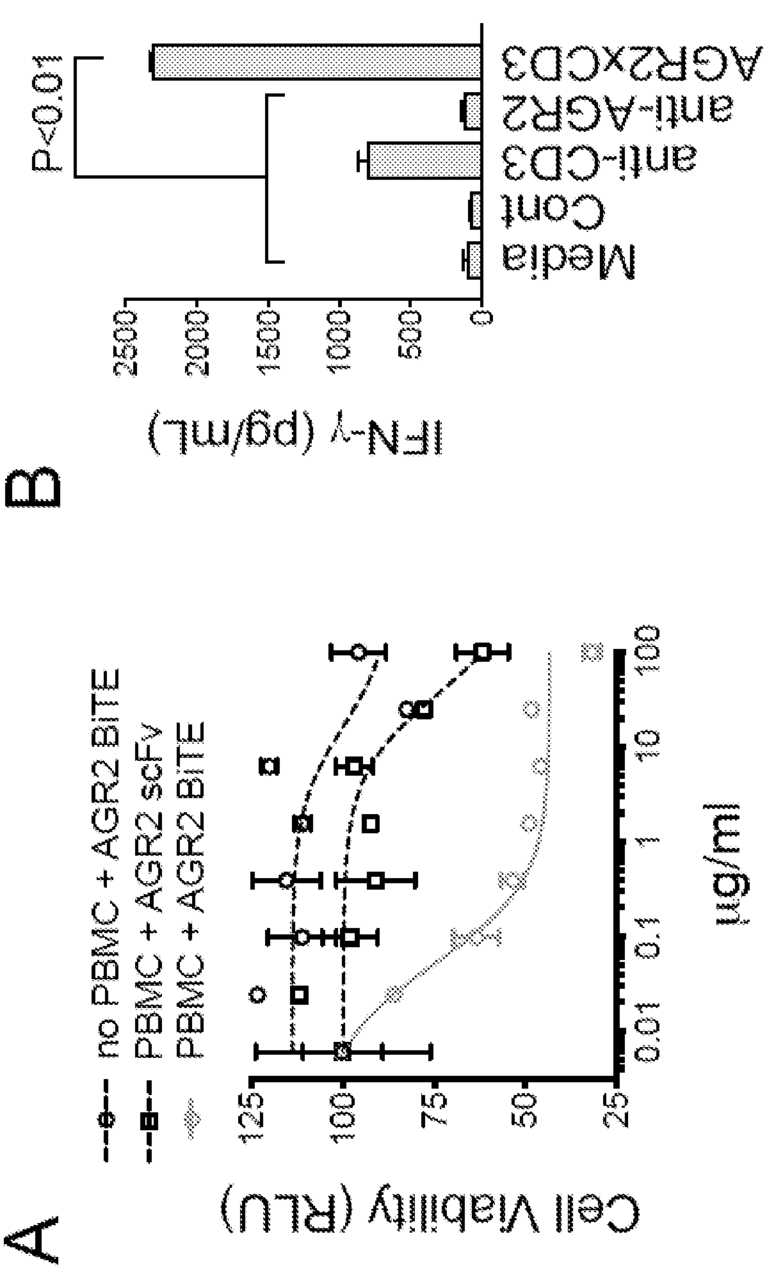
FIGS. 3A-B

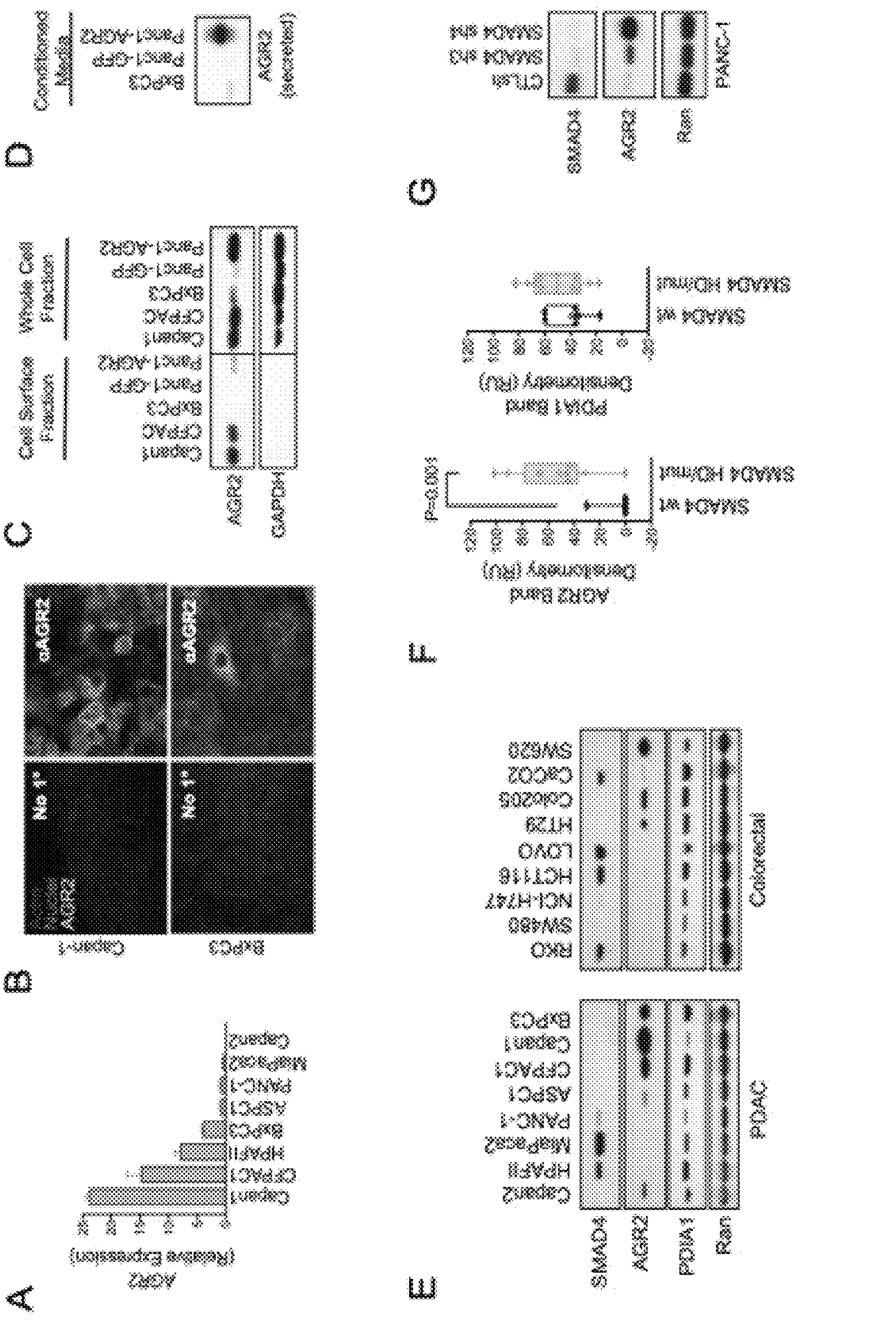
FIGS. 4A-G

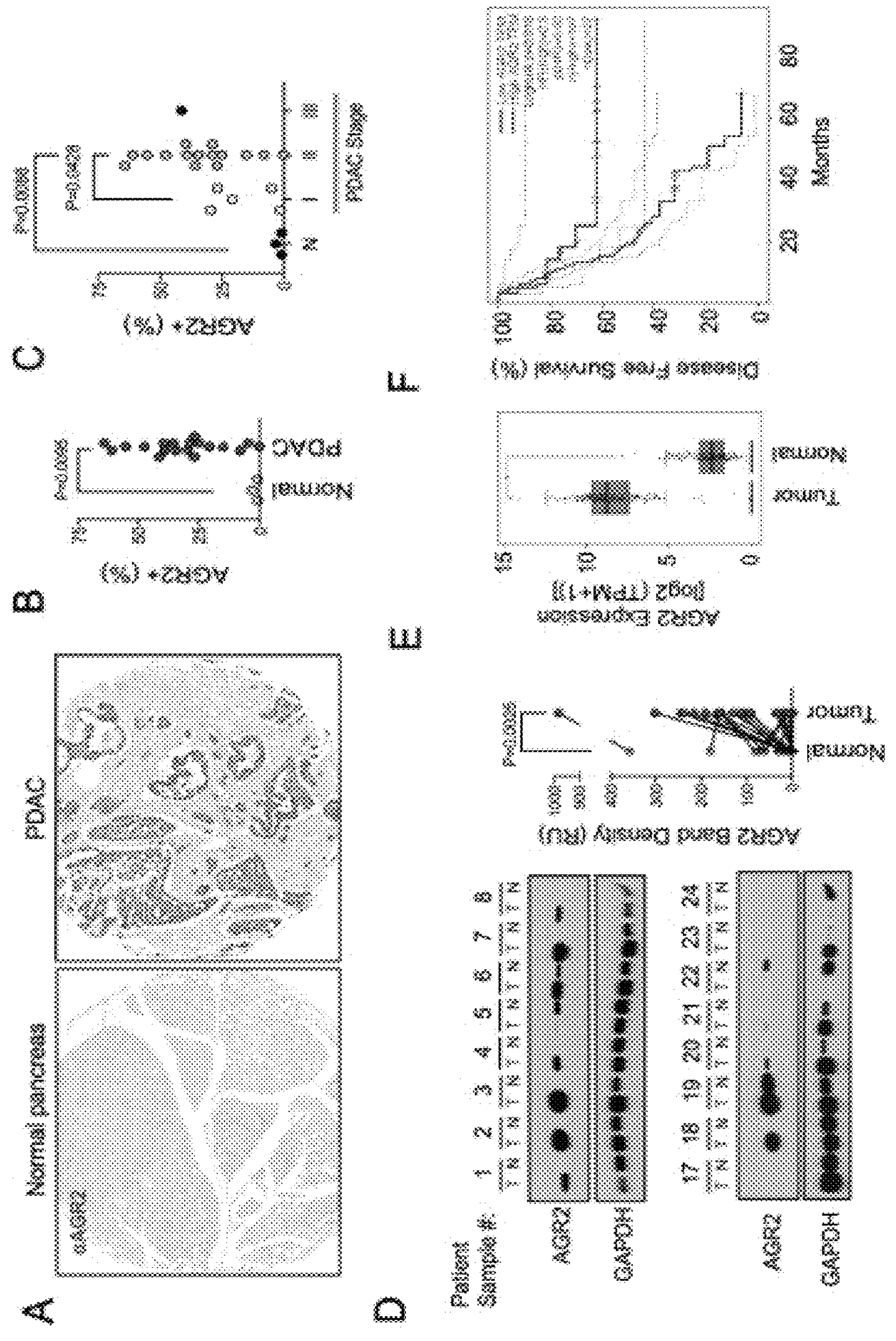
FIGS. 5A-F

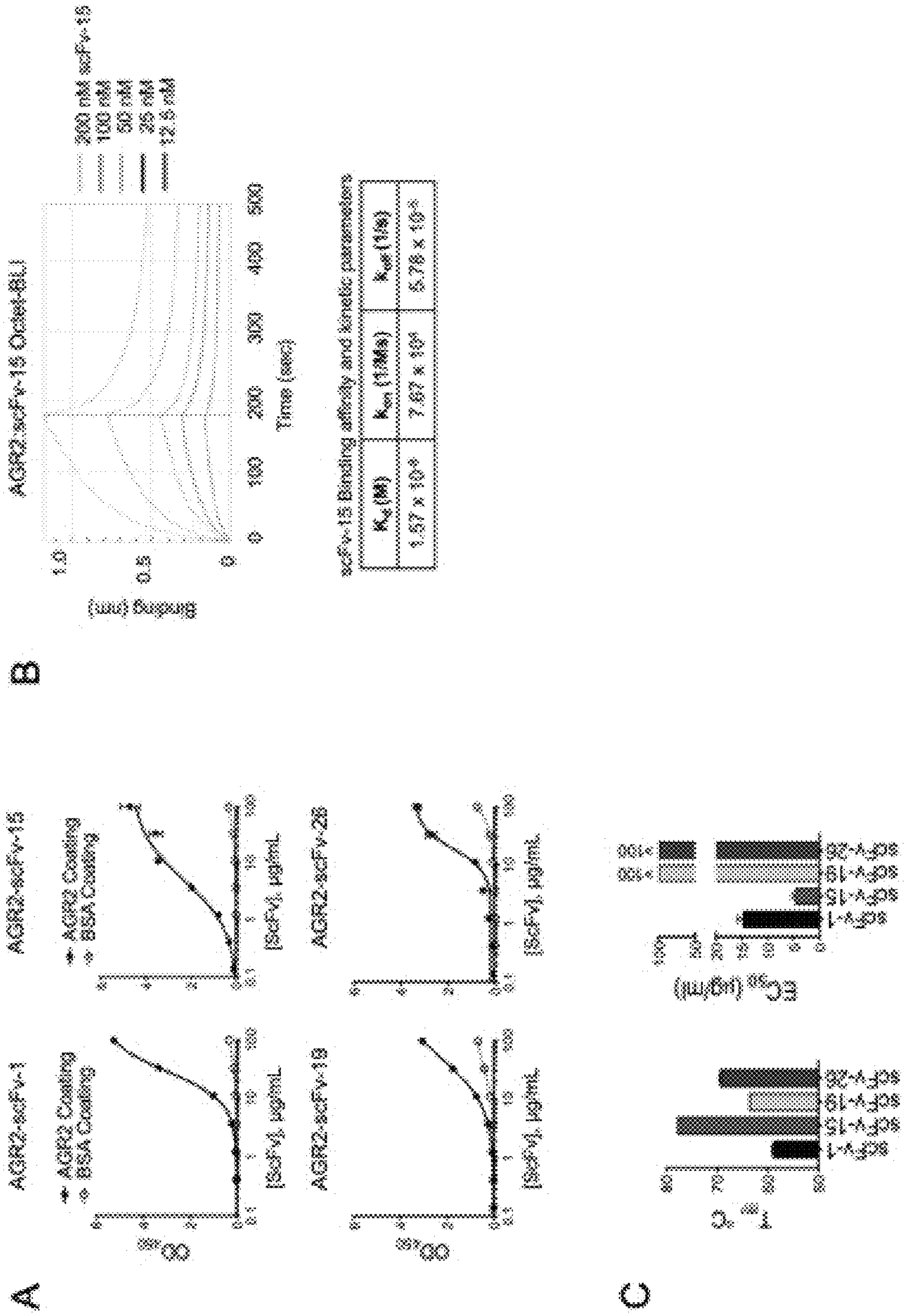
FIGS. 6A-C

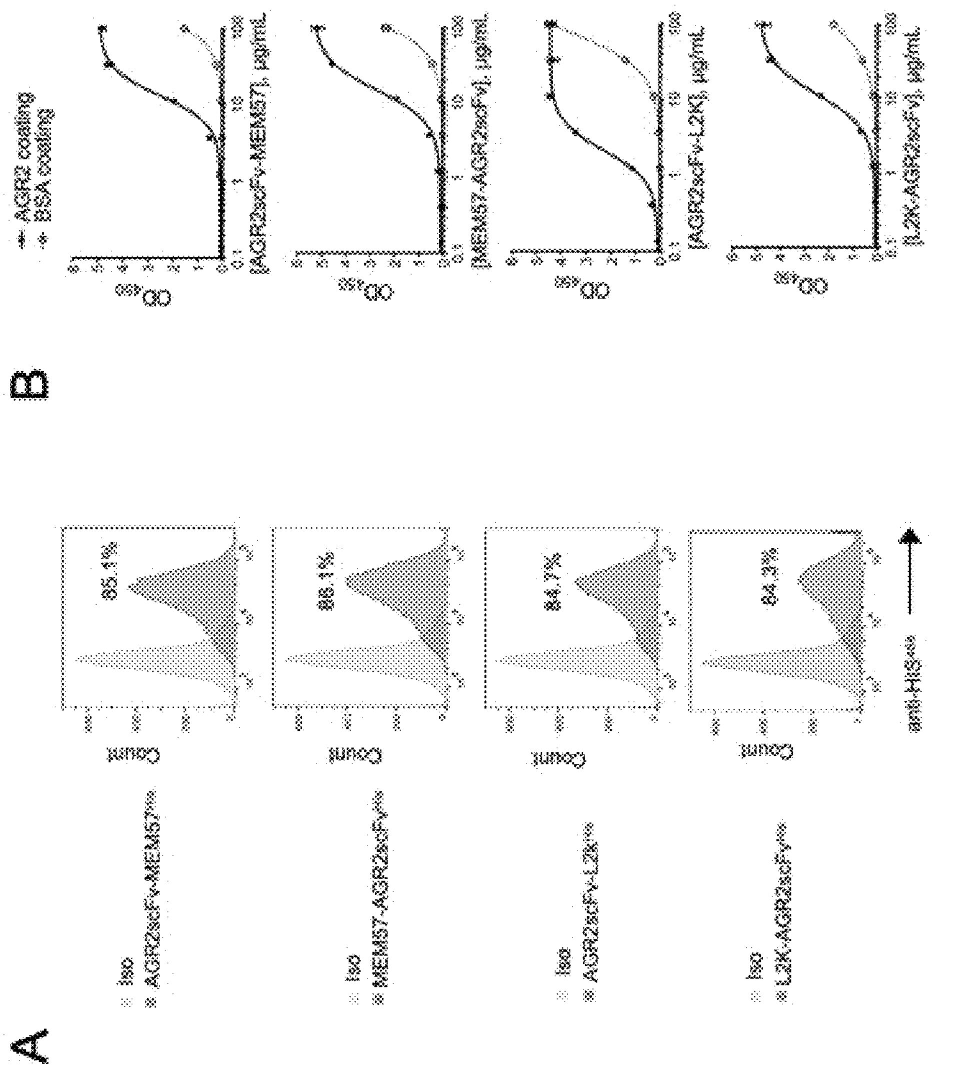
FIGS. 7A-B

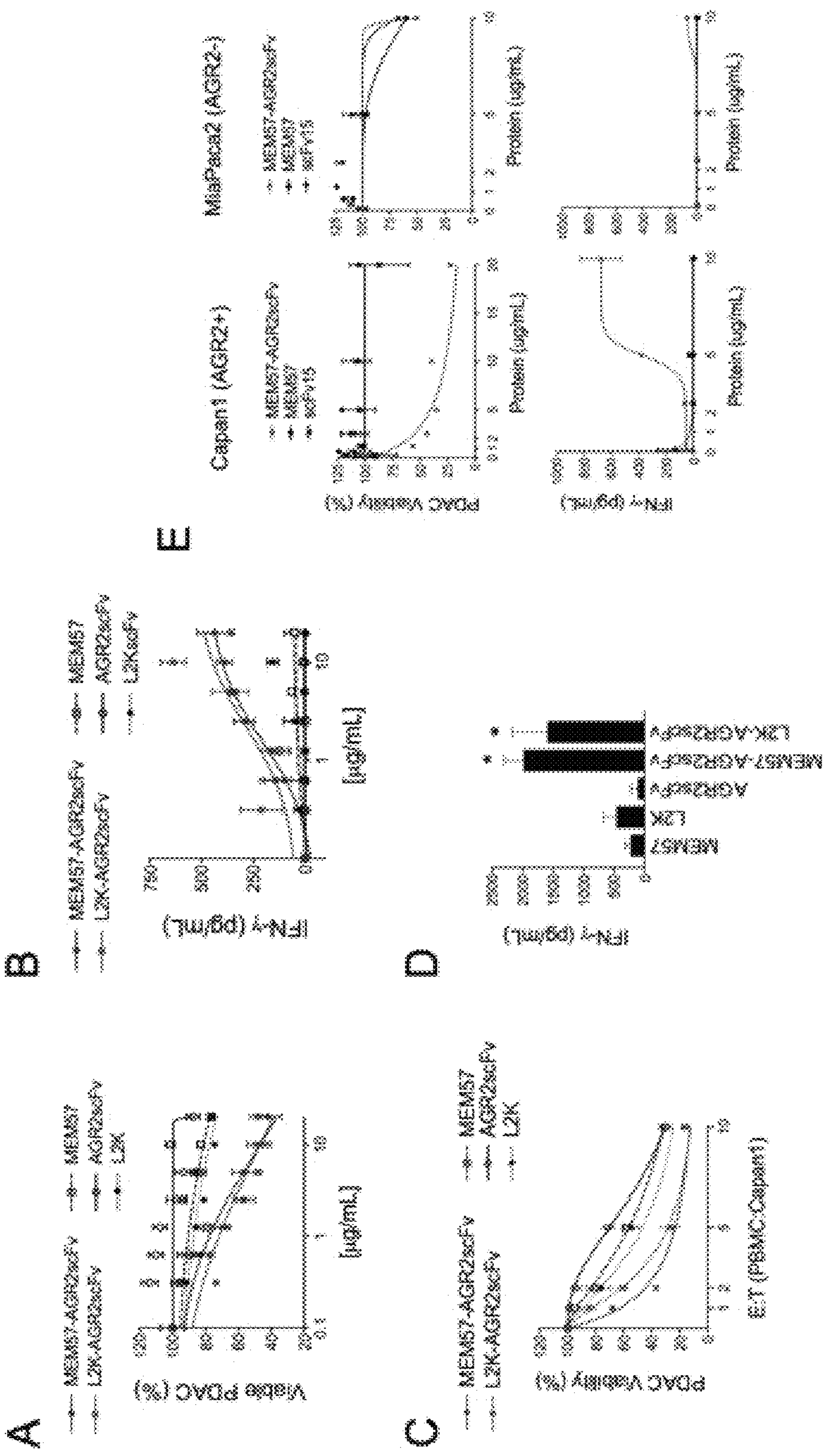
FIGS. 8A-E

SEQUENCE LISTING

```
<160> NUMBER OF SEQ ID NOS: 26

<210> SEQ ID NO 1
<211> LENGTH: 717
<212> TYPE: DNA
<213> ORGANISM: Artificial sequence
<220> FEATURE:
<223> OTHER INFORMATION: Synthetic antibody

<400> SEQUENCE: 1

gaggtgcagc tgttggagtc tgggggaggc ttggtacagc ctggggggtc cctgagactc      60

tcctgtgcag cctctggatt cacctttagc agctatgcca tgagctgggt ccgccaggct     120

ccagggaagg ggctggagtg ggtctcaggt atttagagta cgggtgcgtt gacagcttac     180

gcagactccg tgaagggccg gttcaccatc tccagagaca attccaagaa cacgctgtat     240

ctgcaaatga acagcctgag agccgaggac acggccgtat attactgtgc gaaattggct     300

tagacgtttg actactgggg ccagggaacc ctggtcaccg tctcgagcgg tggaggcggt     360

tcaggcggag gtggcagcgg cggtggcggg tcgacggaca tccagatgac ccagtctcca     420

tcttccctgt ctgcatctgt aggagacaga gtcaccatca cttgccgggc aagtcagagc     480

attagcagct atttaaattg gtatcagcag aaaccaggga aagcccctaa gctcctgatc     540

tatcgggcat cctccttgca aagtggggtc ccatcaaggt tcagtggcag tggatctggg     600
```

acagatttca ctctcaccat cagcagtctg caacctgaag attttgcaac ttactactgt 660
caacagactc ggaggctgcc tgtgacgttc ggccaaggga ccaaggtgga aatcaaa 717

<210> SEQ ID NO 2
<211> LENGTH: 717
<212> TYPE: DNA
<213> ORGANISM: Artificial sequence
<220> FEATURE:
<223> OTHER INFORMATION: Synthetic antibody

<400> SEQUENCE: 2
gaggtgcagc tgttggagtc tgggggaggc ttggtacagc ctggggggtc cctgagactc 60
tcctgtgcag cctctggatt cacctttagc agctatgcca tgagctgggt ccgccaggct 120
ccagggaagg ggctggagtg ggtctcaggt atttctgctc agggtgcgca tacaacgtac 180
gcagactccg tgaagggcag gttcaccatc tccagagaca attccaagaa cacgctgtat 240
ctgcaaatga acagcctgag agccgaggac acggccgtat attactgtgc gaaaacgtat 300
aaggggtttg actactgggg ccagggaacc ctggtcaccg tctcgagcgg tggaggcggt 360
tcaggcggag gtggcagcgg cggtggcggg tcgacggaca tccagatgac ccagtctcca 420
tcctccctgt ctgcatctgt aggagacaga gtcaccatca cttgccgggc aagtcagagc 480
attagcagct atttaaattg gtatcagcag aaaccaggga aagcccctaa gctcctgatc 540
tatagtgcat ccaggttgca aagtggggtc ccatcaaggt tcagtggcag tggatctggg 600
acagatttca ctctcaccat cagcagtctg caacctgaag attttgcaac ttactactgt 660
caacaggggc ggcggatgcc tccgacgttc ggccaaggga ccaaggtgga aatcaaa 717

<210> SEQ ID NO 3
<211> LENGTH: 717
<212> TYPE: DNA
<213> ORGANISM: Artificial sequence
<220> FEATURE:
<223> OTHER INFORMATION: Synthetic antibody

<400> SEQUENCE: 3
cgaggtgcag ctgttggagt ctgggggagg cttggtacag cctggggggt cctgagactc 60
tcctgtgcag cctctggatt cacctttagc agctatgcca tgagctgggt ccgccaggct 120
ccagggaagg ggctggagtg ggtctcagcg attgcgtcgt agggtgtggc tacagggtac 180
gcagactccg tgaagggccg gttcaccatc tccagagaca attccaagaa cacgctgtat 240
ctgcaaatga acagcctgag agccgaggac acggccgtat attactgtgc gaaattggat 300
cagcattttg actactgggg ccagggaacc ctggtcaccg tctcgagcgg tggaggcggt 360
tcaggcggag gtggcagcgg cggtggcggg tcgacggaca tccagatgac ccagtctcca 420
tcctccctgt ctgcatctgt aggagacaga gtcaccatca cttgccgggc aagtcagagc 480
attagcagct atttaaattg gtatcagcag aaaccaggga aagcccctaa gctcctgatc 540
tatcaggcat cccggttgca aagtggggtc ccatcaaggt tcagtggcag tggatctggg 600
acagatttca ctctcaccat cagcagtctg caacctgaag attttgcaac ttactactgt 660
caacaggcga ggcgtctgcc tcttacgttc ggccaaggga ccaaggtgga aatcaaa 717

<210> SEQ ID NO 4
<211> LENGTH: 717
<212> TYPE: DNA
<213> ORGANISM: Artificial sequence
<220> FEATURE:

<223> OTHER INFORMATION: Synthetic antibody

<400> SEQUENCE: 4

```
gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcatct atttagggtc agggtcggat tacacggtac    180

gcagactccg tgaagggccg gttcaccatc tccagagaca attccaagaa cacgctgtat    240

ctgcaaatga acagcctgag agccgaggac acggccgtat attactgtgc gaaacgtgcg    300

attatgtttg actactgggg ccagggaacc ctggtcaccg tctcgagcgg tggaggcggt    360

tcaggcggag gtggcagcgg cggtggcggg tcgacggaca tccagatgac ccagtctcca    420

tcctccctgt ctgcatctgt aggagacaga gtcaccatca cttgccgggc aagtcagagc    480

attagcagct atttaaattg gtatcagcag aaaccaggga aagcccctaa gctcctgatc    540

tatcatgcat ccctgttgca aagtggggtc ccatcaaggt tcagtggcag tggatctggg    600

acagatttca ctctcaccat cagcagtctg caacctgaag attttgcaac ttactactgt    660

caacaggcta ggtattggcc tctgacgttc ggccaaggga ccaaggtgga aatcaaa       717
```

<210> SEQ ID NO 5
<211> LENGTH: 239
<212> TYPE: PRT
<213> ORGANISM: Artificial sequence
<220> FEATURE:
<223> OTHER INFORMATION: Synthetic antibody

<400> SEQUENCE: 5

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Gln Ser Thr Gly Ala Leu Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ala Gln Thr Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Arg Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Thr Arg
    210                 215                 220
```

Arg Leu Pro Val Thr Phe Gly Gln Gly Thr Lys Val Glu Ile Lys
225 230 235

<210> SEQ ID NO 6
<211> LENGTH: 239
<212> TYPE: PRT
<213> ORGANISM: Artificial sequence
<220> FEATURE:
<223> OTHER INFORMATION: Synthetic antibody

<400> SEQUENCE: 6

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Gly Ile Ser Ala Gln Gly Ala His Thr Thr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Thr Tyr Lys Gly Phe Asp Tyr Trp Gly Gln Gly Thr Leu Val
100 105 110

Thr Val Ser Ser Gly Gly Gly Gly Ser Gly Gly Gly Gly Ser Gly Gly
115 120 125

Gly Gly Ser Thr Asp Ile Gln Met Thr Gln Ser Pro Ser Ser Leu Ser
130 135 140

Ala Ser Val Gly Asp Arg Val Thr Ile Thr Cys Arg Ala Ser Gln Ser
145 150 155 160

Ile Ser Ser Tyr Leu Asn Trp Tyr Gln Gln Lys Pro Gly Lys Ala Pro
165 170 175

Lys Leu Leu Ile Tyr Ser Ala Ser Arg Leu Gln Ser Gly Val Pro Ser
180 185 190

Arg Phe Ser Gly Ser Gly Ser Gly Thr Asp Phe Thr Leu Thr Ile Ser
195 200 205

Ser Leu Gln Pro Glu Asp Phe Ala Thr Tyr Tyr Cys Gln Gln Gly Arg
210 215 220

Arg Met Pro Pro Thr Phe Gly Gln Gly Thr Lys Val Glu Ile Lys
225 230 235

<210> SEQ ID NO 7
<211> LENGTH: 239
<212> TYPE: PRT
<213> ORGANISM: Artificial sequence
<220> FEATURE:
<223> OTHER INFORMATION: Synthetic antibody

<400> SEQUENCE: 7

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ala Ser Gln Gly Val Ala Thr Gly Tyr Ala Asp Ser Val

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Asp Gln His Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Gln Ala Ser Arg Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ala Arg
    210                 215                 220

Arg Leu Pro Leu Thr Phe Gly Gln Gly Thr Lys Val Glu Ile Lys
225                 230                 235


<210> SEQ ID NO 8
<211> LENGTH: 239
<212> TYPE: PRT
<213> ORGANISM: Artificial sequence
<220> FEATURE:
<223> OTHER INFORMATION: Synthetic antibody

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Gln Gly Gln Gly Arg Ile Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ala Ile Met Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr His Ala Ser Leu Leu Gln Ser Gly Val Pro Ser
```

```
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ala Arg
    210                 215                 220

Tyr Trp Pro Leu Thr Phe Gly Gln Gly Thr Lys Val Glu Ile Lys
225                 230                 235


<210> SEQ ID NO 9
<211> LENGTH: 5
<212> TYPE: PRT
<213> ORGANISM: Artificial sequence
<220> FEATURE:
<223> OTHER INFORMATION: Synthetic antibody

<400> SEQUENCE: 9

Ser Tyr Ala Met Ser
1               5


<210> SEQ ID NO 10
<211> LENGTH: 20
<212> TYPE: PRT
<213> ORGANISM: Artificial sequence
<220> FEATURE:
<223> OTHER INFORMATION: Synthetic antibody

<400> SEQUENCE: 10

Gly Ile Gln Ser Thr Gly Ala Leu Thr Ala Tyr Ala Asp Ser Val Lys
1               5                   10                  15

Gly Arg Phe Thr
            20


<210> SEQ ID NO 11
<211> LENGTH: 7
<212> TYPE: PRT
<213> ORGANISM: Artificial sequence
<220> FEATURE:
<223> OTHER INFORMATION: Synthetic antibody

<400> SEQUENCE: 11

Leu Ala Gln Thr Phe Asp Tyr
1               5


<210> SEQ ID NO 12
<211> LENGTH: 20
<212> TYPE: PRT
<213> ORGANISM: Artificial sequence
<220> FEATURE:
<223> OTHER INFORMATION: Synthetic antibody

<400> SEQUENCE: 12

Gly Ile Ser Ala Gln Gly Ala His Thr Thr Tyr Ala Asp Ser Val Lys
1               5                   10                  15

Gly Arg Phe Thr
            20


<210> SEQ ID NO 13
<211> LENGTH: 7
<212> TYPE: PRT
<213> ORGANISM: Artificial sequence
<220> FEATURE:
<223> OTHER INFORMATION: Synthetic antibody

<400> SEQUENCE: 13
```

```
Thr Tyr Lys Gly Phe Asp Tyr
1               5


<210> SEQ ID NO 14
<211> LENGTH: 20
<212> TYPE: PRT
<213> ORGANISM: Artificial sequence
<220> FEATURE:
<223> OTHER INFORMATION: Synthetic antibody

<400> SEQUENCE: 14

Ala Ile Ala Ser Gln Gly Val Ala Thr Gly Tyr Ala Asp Ser Val Lys
1               5                   10                  15

Gly Arg Phe Thr
            20


<210> SEQ ID NO 15
<211> LENGTH: 7
<212> TYPE: PRT
<213> ORGANISM: Artificial sequence
<220> FEATURE:
<223> OTHER INFORMATION: Synthetic antibody

<400> SEQUENCE: 15

Leu Asp Gln His Phe Asp Tyr
1               5


<210> SEQ ID NO 16
<211> LENGTH: 20
<212> TYPE: PRT
<213> ORGANISM: Artificial sequence
<220> FEATURE:
<223> OTHER INFORMATION: Synthetic antibody

<400> SEQUENCE: 16

Ser Ile Gln Gly Gln Gly Arg Ile Thr Arg Tyr Ala Asp Ser Val Lys
1               5                   10                  15

Gly Arg Phe Thr
            20


<210> SEQ ID NO 17
<211> LENGTH: 7
<212> TYPE: PRT
<213> ORGANISM: Artificial sequence
<220> FEATURE:
<223> OTHER INFORMATION: Synthetic antibody

<400> SEQUENCE: 17

Arg Ala Ile Met Phe Asp Tyr
1               5


<210> SEQ ID NO 18
<211> LENGTH: 6
<212> TYPE: PRT
<213> ORGANISM: Artificial sequence
<220> FEATURE:
<223> OTHER INFORMATION: Synthetic antibody

<400> SEQUENCE: 18

Ile Ser Ser Tyr Leu Asn
1               5


<210> SEQ ID NO 19
<211> LENGTH: 9
<212> TYPE: PRT
<213> ORGANISM: Artificial sequence
```

<220> FEATURE:
<223> OTHER INFORMATION: Synthetic antibody

<400> SEQUENCE: 19

Ile Tyr Arg Ala Ser Ser Leu Gln Ser
1 5

<210> SEQ ID NO 20
<211> LENGTH: 9
<212> TYPE: PRT
<213> ORGANISM: Artificial sequence
<220> FEATURE:
<223> OTHER INFORMATION: Synthetic antibody

<400> SEQUENCE: 20

Gln Gln Thr Arg Arg Leu Pro Val Thr
1 5

<210> SEQ ID NO 21
<211> LENGTH: 9
<212> TYPE: PRT
<213> ORGANISM: Artificial sequence
<220> FEATURE:
<223> OTHER INFORMATION: Synthetic antibody

<400> SEQUENCE: 21

Ile Tyr Ser Ala Ser Arg Leu Gln Ser
1 5

<210> SEQ ID NO 22
<211> LENGTH: 9
<212> TYPE: PRT
<213> ORGANISM: Artificial sequence
<220> FEATURE:
<223> OTHER INFORMATION: Synthetic antibody

<400> SEQUENCE: 22

Gln Gln Gly Arg Arg Met Pro Pro Thr
1 5

<210> SEQ ID NO 23
<211> LENGTH: 9
<212> TYPE: PRT
<213> ORGANISM: Artificial sequence
<220> FEATURE:
<223> OTHER INFORMATION: Synthetic antibody

<400> SEQUENCE: 23

Ile Tyr Gln Ala Ser Arg Leu Gln Ser
1 5

<210> SEQ ID NO 24
<211> LENGTH: 9
<212> TYPE: PRT
<213> ORGANISM: Artificial sequence
<220> FEATURE:
<223> OTHER INFORMATION: Synthetic antibody

<400> SEQUENCE: 24

Gln Gln Ala Arg Arg Leu Pro Leu Thr
1 5

<210> SEQ ID NO 25
<211> LENGTH: 9
<212> TYPE: PRT
<213> ORGANISM: Artificial sequence
<220> FEATURE:

-continued

```
<223> OTHER INFORMATION: Synthetic antibody

<400> SEQUENCE: 25

Ile Tyr His Ala Ser Leu Leu Gln Ser
1               5


<210> SEQ ID NO 26
<211> LENGTH: 9
<212> TYPE: PRT
<213> ORGANISM: Artificial sequence
<220> FEATURE:
<223> OTHER INFORMATION: Synthetic antibody

<400> SEQUENCE: 26

Gln Gln Ala Arg Tyr Trp Pro Leu Thr
1               5
```

AGR2Xcd3 BISPECIFIC ENGAGER FOR THE TREATMENT OF CANCER

PRIORITY CLAIM

This application is an International Application of PCT/US2022/070009 filed Jan. 4, 2022, which claims benefit of priority to U.S. Provisional Application Ser. No. 63/134,093, filed Jan. 5, 2021, the entire contents of both of which are hereby incorporated by reference.

Pursuant to 37 C.F.R. 1.821(c), a sequence listing is submitted herewith as an ASCII compliant text file named "MESCP0128WO_ST25.txt", created on Jan. 3, 2022 and having a size of 18,859 bytes. The content of the aforementioned file is hereby incorporated by reference in its entirety.

BACKGROUND

1. Field of the Disclosure

The present disclosure relates generally to the fields of medicine, immunology and oncology. More particular, the disclosure relates to human antibodies binding to AGR2.

2. Background

Pancreatic cancer accounted for 56,700 new cancer cases and 45,700 deaths in 2019 along with the lowest 5-year survival rate of all cancers at only 9% (Seigel et al., 2019). PDAC, the most common malignancy originating in the pancreas, is predicted to be the second most deadly form of cancer by 2030 behind only lung cancer (Rahib et al., 2014). Standard of care treatments lack efficacy and have remained largely unchanged over the past several decades. These include surgical resection and adjuvant gemcitabine or FOLFIRINOX (Oettle et al., 2013; 2007; Control et al., 2011; 2018). Surgery is the only path to a cure, although >50% of patients present with stage IV disease that has already metastasized (Siegel et al., 2014), and for these patients surgery is palliative at best. Newer agents, like the EGFR inhibitor erlotinib and albumin-bound paclitaxel (nabpaclitaxel) provide only marginal benefit (Sinn et al., 2017; Moore et al., 2007; Manji et al., 2017; Von Hoff et al., 2013). As for immunotherapy, although the PD-1 checkpoint inhibitor pembrolizumab/KETRUDA® is effective in patients with DNA mismatch repair (MMR) deficiency (Le et al., 2017; Boyiadzis et al., 2018), this molecular designation applies to <1% of PDAC patients.14 Indeed, clinical trials have shown almost zero objective responses in PDAC patients enrolled in PD-1/PD-L1 checkpoint inhibitor clinical trials (Ott et al., 2019; Brahmer et al., 2012). This is due, in theory, to immunosuppressive forces within the PDAC tumor microenvironment (TME), including immunosuppressive regulatory T cells (Tregs) and M2 macrophages, that are observed in patient samples and genetically engineered mouse models of PDAC (Clark et al., 2007; Hiraoka et al., 2006; Hu et al., 2016). Thus, PDAC has been labeled as an immunologically "cold" tumor type. Therefore, there is a pressing need for new treatment approaches for this disease, particularly those that harness the power of the immune system to increase anti-tumor T cell responses.

Anterior Gradient 2 (AGR2): AGR2 (PDIA17) is a member of the protein disulfide isomerase (PDI) family, which plays a key role in protein folding by introducing and isomerizing disulfide bonds in newly synthesized proteins. Leukogene Therapeutics, Inc. (LTI) is a leader in the field of PDI research and is commercializing a first-in-class orally bioavailable inhibitor of PDI for the treatment of hematological malignancies. AGR2 shares homology with the Xenopus Anterior Gradient-2 (XAG2) gene, which is secreted by the cement gland in *Xenopus laevis* where it orchestrates embryonic development by directing the polarization of the anterior dorsal ectoderm (Sive et al., 1989; Aberger et al., 1998). In humans, AGR2 expression is upregulated in several human cancers and is linked to increased progression and metastatic spread. In PDAC, we observed intense immunohistochemical staining in PDAC but not normal pancreas tissue using tissue microarrays and human cell lines, which is consistent with the observations of other groups (Riener et al., 2009; Dumartin et al., 2011) AGR2 is a unique member of the PDI family as it is expressed as an intracellular protein but is also secreted from the cell where it associates with the cell membrane and surrounding milieu. AGR2 is an appealing drug target in PDAC. It is an early biomarker of pancreatic intraepithelial neoplasia (PanIN) and PDAC that is secreted into blood serum and pancreatic fluid (Chen et al., 2010; Le Large et al., 2017), as well as the cell culture supernatant of PDAC cell lines (Dumnartin et al., 2011; Ramachandran et al., 2008). Studies have also shown that it plays a causal role in the initiation and progression of PDAC in mouse models (Dumartin et al., 2017). A number of pro-oncogenic functions have been ascribed to AGR2, including the promotion of cell survival, invasion, increased metastatic potential, and resistance to therapy (Di Mar et al., 2014; Ma et al., 2017; Wang et al., 2008). AGR2 is up-regulated downstream of KRAS G12D mutation in PDAC (Boj et al., 2015) and is repressed by SMAD4 (Norris et al., 2013), which is lost by mutation or homozygous deletion in roughly ⅓ of PDAC patients (Singh et al., 2012).

SUMMARY

Thus, in accordance with the present disclosure, there is provided a method of detecting an AGR2-expressing or overexpressing cancer in a subject comprising (a) contacting a sample from said subject with an antibody, single chain antibody or antibody fragment having clone-paired heavy and light chain CDR sequences from Tables 3 and 4, respectively; and (b) detecting an AGR2-expression or overexpressing cancer cells in said sample by binding of said antibody, single chain antibody or antibody fragment to a cancer cell in said sample. The sample may be a body fluid such as blood, sputum, tears, saliva, mucous or serum, semen, cervical or vaginal secretions, amniotic fluid, placental tissues, urine, exudate, transudate, or may be tissue scrapings or feces. Detection may comprise ELISA, RIA, lateral flow assay or Western blot. The method may further comprise performing steps (a) and (b) a second time and determining a change in AGR2 antigen levels or cancer cells as compared to the first assay.

The antibody, single chain antibody or antibody fragment may be encoded by variable sequences as set forth in Table 1, may be encoded by light and heavy chain variable sequences having 70%, 80%, or 90% identity to variable sequences as set forth in Table 1, or may be encoded by light and heavy chain variable sequences having 95% identity to sequences as set forth in Table 1. The antibody, single chain antibody or antibody fragment may comprise light and heavy chain variable sequences according to sequences from Table 2, may comprise light and heavy chain variable sequences having 70%, 80% or 90% identity to sequences from Table 2, or may comprise light and heavy chain variable sequences having 95% identity to sequences from Table 2. The antibody fragment may be a recombinant scFv (single chain fragment variable) antibody, Fab fragment, $F(ab')_2$ fragment, or Fv fragment.

In another embodiment, there is provided a method of treating a subject having an AGR2-expressing or overexpressing cancer comprising delivering to said subject an antibody, single chain antibody or antibody fragment having clone-paired heavy and light chain CDR sequences from Tables 3 and 4, respectively. Delivering may comprises antibody, single chain antibody or antibody fragment administration, or genetic delivery with an RNA or DNA sequence or vector encoding the antibody or antibody fragment.

The antibody, single chain antibody or antibody fragment may be encoded by variable sequences as set forth in Table 1, may be encoded by light and heavy chain variable sequences having 70%, 80%, or 90% identity to variable sequences as set forth in Table 1, or may be encoded by light and heavy chain variable sequences having 95% identity to sequences as set forth in Table 1. The antibody, single chain antibody or antibody fragment may comprise light and heavy chain variable sequences according to sequences from Table 2, may comprise light and heavy chain variable sequences having 70%, 80% or 90% identity to sequences from Table 2, or may comprise light and heavy chain variable sequences having 95% identity to sequences from Table 2. The antibody fragment may be a recombinant scFv (single chain fragment variable) antibody, Fab fragment, $F(ab')_2$ fragment, or Fv fragment.

The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, LALA-PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The bispecific antibody may be a Bi-specific T-cell engager, such as one that comprises an Fc portion mutated to alter (eliminate or enhance) FcR interactions, to increase half-life and/or increase therapeutic efficacy, such as a LALA, LALA-PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern.

In yet another embodiment, there is provided an antibody wherein the antibody, single chain antibody or antibody fragment is characterized by heavy and light chain CDR sequences from Tables 3 and 4, respectively. The antibody, single chain antibody or antibody fragment may be encoded by variable sequences as set forth in Table 1, may be encoded by light and heavy chain variable sequences having 70%, 80%, or 90% identity to variable sequences as set forth in Table 1, or may be encoded by light and heavy chain variable sequences having 95% identity to sequences as set forth in Table 1. The antibody, single chain antibody or antibody fragment may comprise light and heavy chain variable sequences according to sequences from Table 2, may comprise light and heavy chain variable sequences having 70%, 80% or 90% identity to sequences from Table 2, or may comprise light and heavy chain variable sequences having 95% identity to sequences from Table 2. The antibody fragment may be a recombinant scFv (single chain fragment variable) antibody, Fab fragment, $F(ab')_2$ fragment, or Fv fragment. The antibody, single chain antibody or antibody fragment may further comprise a cell penetrating peptide and/or is an intrabody.

The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, LALA-PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The bispecific antibody may be a Bi-specific T-cell engager, such as one that comprises an Fc portion mutated to alter (eliminate or enhance) FcR interactions, to increase half-life and/or increase therapeutic efficacy, such as a LALA, LALA-PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern.

In a further embodiment, there is provided a hybridoma or engineered cell encoding an antibody, single chain antibody or antibody fragment wherein the antibody, single chain antibody or antibody fragment is characterized by clone-paired heavy and light chain CDR sequences from Tables 3 and 4, respectively. The antibody, single chain antibody or antibody fragment may be encoded by variable sequences as set forth in Table 1, may be encoded by light and heavy chain variable sequences having 70%, 80%, or 90% identity to variable sequences as set forth in Table 1, or may be encoded by light and heavy chain variable sequences having 95% identity to sequences as set forth in Table 1. The antibody, single chain antibody or antibody fragment may comprise light and heavy chain variable sequences according to sequences from Table 2, may comprise light and heavy chain variable sequences having 70%, 80% or 90% identity to sequences from Table 2, or may comprise light and heavy chain variable sequences having 95% identity to sequences from Table 2. The antibody fragment may be a recombinant scFv (single chain fragment variable) antibody, Fab fragment, $F(ab')_2$ fragment, or Fv fragment. The antibody, single chain antibody or antibody fragment may further comprise a cell penetrating peptide and/or is an intrabody.

The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, LALA-PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The bispecific antibody may be a Bi-specific T-cell engager, such as one that comprises an Fc portion mutated to alter (eliminate or enhance) FcR interactions, to increase half-life and/or increase therapeutic efficacy, such as a LALA, LALA-PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern.

In yet a further embodiment, there is provided a vaccine formulation comprising one or more full length or single chain antibodies or antibody fragments characterized by clone-paired heavy and light chain CDR sequences from Tables 3 and 4, respectively. The one or more antibody, single chain antibody or antibody fragment may be encoded by variable sequences as set forth in Table 1, may be encoded by light and heavy chain variable sequences having 70%, 80%, or 90% identity to variable sequences as set forth in Table 1, or may be encoded by light and heavy chain variable sequences having 95% identity to sequences as set forth in Table 1. The one or more antibody, single chain antibody or antibody fragment may comprise light and heavy chain variable sequences according to sequences from Table 2, may comprise light and heavy chain variable sequences having 70%, 80% or 90% identity to sequences from Table 2, or may comprise light and heavy chain variable sequences having 95% identity to sequences from Table 2. The antibody fragment may be a recombinant scFv (single chain fragment variable) antibody, Fab fragment, $F(ab')_2$ fragment, or Fv fragment. The antibody, single chain antibody or antibody fragment may further comprise a cell penetrating peptide and/or is an intrabody.

The one or more antibody may be an IgG, or a recombinant IgG antibody or antibody fragment comprising an Fc portion mutated to alter (eliminate or enhance) FcR interactions, to increase half-life and/or increase therapeutic efficacy, such as a LALA, LALA-PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. The one or more antibody may be a chimeric antibody or a bispecific antibody. The one or more bispecific antibody may be a Bi-specific T-cell engager, such as one that comprises an Fc portion mutated to alter (eliminate or enhance) FcR interactions, to increase half-life and/or increase therapeutic efficacy, such as a LALA, LALA-PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern.

Also provided is vaccine formulation comprising one or more expression vectors encoding a first antibody, single chain antibody or antibody fragment as described herein. The expression vector(s) may be Sindbis virus or VEE vector(s), and/or may be formulated for delivery by needle injection, jet injection, or electroporation, and/or may further comprise one or more expression vectors encoding for a second antibody, single chain antibody or antibody fragment, such as a distinct antibody or antibody fragment as defined herein.

Additionally, there is provided a chimeric antigen receptor comprising:

(i) an ectodomain comprising single chain antibody variable region having clone-paired heavy and light chain CDR sequences from Tables 3 and 4, respectively, with a flexible hinge attached at the C-terminus of said single chain antibody variable region;

(ii) a transmembrane domain; and (iii) an endodomain, wherein said endodomain comprises a signal transduction function when said single-chain antibody variable region is engaged with MUC1.

The transmembrane and endodomains may be derived from the same molecule. The endodomain amy comprise a CD3-zeta domain or a high affinity FcRI.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-B. Anti-AGR2 scFv clone-15. (FIG. 1A) Clone-15 binding to AGR2 or control (BSA) plates is shown by ELISA. (FIG. 1B) Thermodynamic stability data for anti-AGR2 scFvs shows that clone-15 is the most stable.

FIGS. 2A-D. Human and mouse AGR2xCD3 BiTE constructs. (FIG. 2A) Binding of human targeted AGR2xCD3 BiTE to AGR2 is shown by ELISA. (FIG. 2B) Binding of human targeted AGR2xCD3 BiTE to human Jurkat T cells is shown by flow cytometry. A His-tag was cloned into the BiTE for detection with an Alexa488 labeled secondary antibody. (FIG. 2C) Binding of mouse targeted AGR2xCD3 BiTE to AGR2 is shown by ELISA. (FIG. 2D) Binding of mouse targeted mCD3xAGR2 BiTE to mouse EL4 T cells is shown by flow cytometry. Note that the human BiTE (yellow) does not react with mouse T cells.

FIGS. 3A-B. T cell dependent killing of PDAC cells by AGR2xCD3 BITE. (FIG. 3A) AGR2+ Capan1 cells were incubated with human PBMCs (E:T=10:1) and a dose range of the AGR2xCD3 BiTE or the AGR2 scFv clone-15. After 48 hrs, PBMC/T cells were washed away and viability of Capan1 cells was measured. (FIG. 3B) IFN gamma in media from the indicated cultures was measured by ELISA as a surrogate for T cell activation.

FIGS. 4A-G. AGR2 expression in PDAC cell lines. (FIG. 4A) Relative expression of AGR2 mRNA is shown by qRT-PCR in the indicated PDAC cell lines. (FIG. 4B) AGR2 immunofluorescence (green) in Capan1 and BxPC3 cells is shown. Nuclear (blue) and cytoskeletal (red) counterstains were included. (FIG. 4C) Western blots of AGR2 expression from the cell surface and whole cell fractions in different PDAC cell lines is shown. (FIG. 4D) Western blots of secreted AGR2 from conditioned media of different PDAC cell lines is shown. (FIG. 4E) Western blots of SMAD4, AGR2, and PDIA1 in different PDAC and colorectal cancer cell lines are shown. (FIG. 4F) Densitometry analysis of AGR2 or PDIA1 band intensity from FIG. 4E in SMAD4 WT and SMAD4 homozygous deletion (HD)/mut cell lines is shown. Note the strong correlation between SMAD4 mutation status and AGR2, but not PDIA1. (FIG. 4G) Western blots of SMAD4 and AGR2 from Panc-1 cells with SMAD4 knockdown are shown.

FIGS. 5A-F. AGR2 expression in primary patient PDAC samples. (FIG. 5A) A representative immunohistochemistry (IHC) staining of AGR2 in tissue cores from normal pancreas and PDAC tissues are shown. (FIG. 5B) A tissue microarray (TMA) of normal and PDAC tissue was analyzed for AGR2 expression as in FIG. 5A. The percentage of AGR2 positive epithelial cells was quantified using the Vectra Polaris Imaging System and related analytical software. (FIG. 5C) The percentage of AGR2 positive epithelial cells from PDAC tissues representing the different stages of disease are shown. (FIG. 5D) Western blots of AGR2 from matching primary PDAC patient samples are shown. Samples were harvested from PDAC tumor (T) and normal adjacent (N) pancreatic tissue biopsies. Band densitometry quantification is also provided (right). (FIG. 5E) AGR2 mRNA expression data was mined from TCGA datasets from PDAC tumor and normal pancreatic tissues. F) Disease free survival of patients with low or high AGR2 mRNA expression in PDAC tumors is shown.

FIGS. 6A-C. Biochemical properties of the AGR2-binding scFvs. (FIG. 6A) ELISAs for the indicated anti-AGR2 scFv clones shows specific binding to AGR2 but not BSA (control) coated plates. (FIG. 6B) Octet-Bio-Layer Interferometry (BLI) was used to measure the binding kinetics of anti-AGR2 scFv clone-15 to AGR2. Kinetic parameters are indicated in the table (bottom). (FIG. 6C) Melting temperatures and ELISA $EC_{50}$s of the purified AGR2 scFvs are shown. Melting temperatures of the scFvs were measured using a Tycho NanoTemper Thermophoresis unit. $EC_{50}$ values for each scFv were calculated from the ELISAs in FIG. 6A.

FIG. 7A-B. Binding confirmation of AGR2 bispecific T Cell Engager constructs (BiTEs) to Jurkat T cells and AGR2. (FIG. 7A) Flow cytometry was conducted on Jurkat cells with the indicated AGR2xCD3 BiTEs. 2 μg of BiTE was used and an Alexa Fluor 488 conjugated anti-6x-His antibody was used for detection by flow cytometry. (FIG. 7B) ELISA data shows specific binding of AGR2xCD3 BiTEs to AGR2.

FIGS. 8A-E. In cellulo T cell dependent anti-PDAC activity of AGR2xCD3 BiTE. (FIG. 8A) T cell dependent cytotoxicity assays were conducted using AGR2+ Capan1 PDAC cells co-cultured with naïve human T cells from normal human peripheral blood mononuclear cells (PBMCs) at a 2:1 effector:tumor cell ratio (E:T). Capan1/T cell co-cultures were incubated with a dose range of BiTEs (MEM57-AGR2scFv or L2K-AGR2scFv) or individual anti-CD3 (MEM57 or L2K) or anti-AGR2 (AGR2scFv) scFvs. Capan1-specific cell viability was measured at 48 hrs by washing and aspirating non-adherent T cells. The remaining adherent Capan1 cell viability was measured using the Cell TiterGlo cell viability assay system and a SpectraMax L luminometer. (FIG. 8B) Human IFN-gamma was measured by ELISA in supernatant media from experiments in FIG. 8A. (FIG. 8C) The co-culture system described in FIG. 8A was used with the exception that the E:T ratio was varied from 0.5:1-10:1 with a fixed concentration of 10 μg/mL for the BiTEs or individual anti-CD3 and anti-AGR2 scFvs. Capan1 cell viability is shown and was measured as described in FIG. 8A. (FIG. 8D) Human IFN-gamma ELISA (Invitrogen) from supernatant media from the 5:1 E:T ratio in FIG. 8C. (FIG. 8E) T cell co-culture experiments were conducted with AGR2-positive Capan1 and AGR2-negative MiaPaca2 cells for comparison. Cell viability data (top) and IFN-gamma data (bottom) are shown.

DESCRIPTION OF ILLUSTRATIVE EMBODIMENTS

AGR2 expression is induced in several cancer types, including pancreatic ductal adenocarcinoma (PDAC). The inventors hypothesized that the high expression level of AGR2 in PDAC and its oncogenic function would make it a therapeutic target in PDAC. Furthermore, the suspect that its expression on the surface of PDAC cells and in the TME make it an actionable candidate for immunotherapy.

Thus, the inventors produced a multiple anti-AGR2 antibody single chain variable fragment (scFv) and constructed an AGR2xCD3 BiTE by cloning the novel anti-AGR2 scFv in tandem with an agonistic anti-CD3 scFv derived from the sequence of Orthoclone OKT3. The BiTE can be used as an immunotherapeutic for the treatment of PDAC and other cancers to recruit and activate CD3 positive T cells in AGR2 expressing tumors. The inventors have generated two BiTE molecules. One incorporates the OKT3 scFv which specifically targets human CD3 and the other specifically targets mouse CD3 and uses an scFv derived from the 145-C11 anti-murine CD3 antibody clone.

These and other aspects of the disclosure are described in detail below.

I. AGR2 and Cancer

Anterior gradient protein 2 homolog (AGR-2), also known as secreted cement gland protein XAG-2 homolog, is a protein that in humans is encoded by the AGR2 gene. Anterior gradient homolog 2 was originally discovered in *Xenopus laevis*. In *Xenopus* AGR2 plays a role in cement gland differentiation, but in human cancer cell lines high levels of AGR2 correlate with downregulation of the p53 response, cell migration, and cell transformation. However, there have been other observations that AGR2 can repress growth and proliferation.

The *Xenopus laevis* anterior gradient genes-XAG-1, XAG-2, and XAG-3-were discovered through dissection of different-aged embryos. They become expressed in the anterior region of the dorsal ectoderm in late gastrula embryos. XAG-2 expression gathers at the anterior region of the dorsal ectoderm, and this region corresponds to the cement gland anlage. Many other homologous proteins have been discovered afterwards in *Xenopus*.

AGR2 is the human homolog of XAG-2. It is expressed strongly in tissues that secrete mucus or function as endocrine organs, including the lungs, stomach, colon, prostate and small intestine. Its protein expression has been shown to be regulated by both androgens and estrogens.

AGR2 is a protein disulfide isomerase, with a single CXXS active domain motif for oxidation and reduction reactions. AGR2 forms mixed disulfides in substrates, such as intestinal mucin. AGR2 interacts with Mucin 2 through its thioredoxin-like domain forming a heterodisulfide bond with cysteine residues in MUC2. AGR2 is suggested to play a role in protein folding, and it has a KTEL C-terminal motif similar to KDEL and KVEL endoplasmic reticulum retention sequences.

Agr2 is located on chromosome 7p21, a region that has frequent genetic alterations. It was first identified in estrogen receptor-positive breast cancer cells. Later studies showed elevated levels of AGR2 in adenocarcinomas of the esophagus, pancreas, and prostate. In Barrett's esophagus, Agr2 expression is elevated by over 70 times compared to normal esophageal epithelia. Thus, this protein alone is enough to distinguish Barrett's esophagus, which is linked to esophageal adenocarcinoma, from a normal esophagus.

Varying AGR2 levels exist in different cancers. In breast cancer, high AGR2 expression is correlated with low survival rate. AGR2 levels are elevated in the preneoplastic tissue Barrett's esophagus. AGR2 is also associated with prostate cancer, though lower levels are associated with higher Gleason grades.

In contrast to upregulation of AGR2 in various cancers, downregulation of AGR2 is linked with inflammatory bowel disease and increases in the risk of Crohn's disease and ulcerative colitis. This implies the importance of AGR2 in maintaining epithelial barrier function, which is supported by FOXA1 and FOXA2 molecules (transcription factors for epithelial goblet cells) which can activate the AGR2 promoter.

In breast cancer, AGR2 and estrogen (ER) expression are positively correlated. Approximately 70% of breast cancer patients have breast cancer cells that heavily express ER and progesterone receptors (PgR). These patients are normally treated with endocrine therapy. Tamoxifen, which blocks the binding of estradiol to its receptor, is the standard treatment for ER-positive breast cancer. However, about one third of patients do not respond to this therapy, and increased AGR2 may be one reason.

There is a positive correlation for a higher level of AGR2 expression with poor therapeutic results in ERα-positive breast cancer patients. Agr2 mRNA expression is elevated in in vitro and in vivo studies responding to tamoxifen adjuvant therapy, so AGR2 is likely provides an agonistic effect on tamoxifen. Therefore, AGR2 is a possible predictive biomarker when selecting patients with ER-positive breast cancer to participate this therapy. Although Agr2 mRNA levels are correlated with the tamoxifen therapy response, AGR2 protein levels have yet to be statistically associated with the therapy. A combinatorial therapy using the anastrozole and fulvestrant has been shown to prevent binding of the ER to the Agr2 promoter, and there has been improved prognosis in the patients receiving it, possibly because AGR2 expression in the tumors have been reduced.

What AGR2 does in cancers is poorly understood. In breast cancer, HSP90 is a molecular chaperone expressed in tumor cells when there exists an excess of unfolded protein, and its co-chaperone has been reported to induce expression of AGR2, so AGR2 may be used by the endoplasmic reticulum to assist with protein folding to alleviate proteotoxic stress. AGR2 may help regulate the protein and mRNA levels in a cell overall as well. During late pregnancy and lactation, AGR2 levels peak when milk proteins are produced, and mammary-specific Agr2 knockout mice had downregulated milk protein mRNA expression.

AGR2 is expressed in relatively high levels for prostate cancer patients. Urine sediment tests determined Agr2 transcript levels to be elevated. AGR2 expression was increased in metastatic prostate cancer cells cultured in a bone marrow microenvironment, where intense levels of Agr2 mRNA were detected, suggesting AGR2 is required for bone metastasis of prostate cancer cells. AGR2 transcript levels were lower in metastatic lesions compared to the primary tumor, however. A greater chance of prostate cancer recurrence is linked to relatively lower levels of AGR2.

AGR2 depletion through gene knockdown was shown to result in accumulation of prostate cancer cell lines at the G0/G1 phase of the cell cycle, while forced expression of AGR led to an increase in cell proliferation. AGR2 was determined to be involved in cell adhesion. Agr2-silenced prostate cancer cells had a large decrease in association with fibronectin, lost expression of integrin, and reduced tumor cell migration. In addition to these studies, AGR2 was among a set of genes consistently associated with prostate tumor visibility on MRI in a bioinformatic analysis, the analysis found that more visible tumors harbored more aggressive genetic characteristics. The study also found genes involved with cell-ECM interactions to be altered in aggressive MRI-visible tumors, potentially reflecting AGR2's association with cellular adhesion and integrin signaling.

AGR2 mRNA was discovered to be increased in precancerous lesions and neoplastic cells of pancreatic tumors and cancer cell lines. Transient silencing of AGR2 by small interfering RNA and short hairpin RNA significantly reduces cell proliferation and invasion while increasing the effectiveness of gemcitabine treatment in pancreatic cancer cell lines in vitro, indicating that AGR2 can help pancreatic cancer cells survive and protect tumors from chemotherapeutic treatments for pancreatic cancer. This is critical because pancreatic cancer is well recognized as being highly resistant to therapeutics, and five-year survival rates for pancreatic cancer are extremely low.

AGR2 protein has been demonstrated to interact with C4.4A and DAG-1 proteins which are associated with metastasis formation since these transmembrane proteins are involved in cell and matrix interactions between cancer and normal cells. AGR2 is able to suppress p53 activity by preventing phosphorylation after DNA damage. AGR2 has been shown to bind to Reptin, a tumor repressor, in the nucleus.

II. Monoclonal Antibodies and Production Thereof

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In particular embodiments, the antibody is purified: (1) to greater than 95% by weight of antibody as determined by the Lowry method, and most particularly more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the alpha and gamma chains and four $C_H$ domains for mu and isotypes. Each L chain has at the N-terminus, a variable region ($V_L$) followed by a constant domain ($C_L$) at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa and lambda based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha, delta, epsilon, gamma and mu, respectively. They gamma and alpha classes are further divided into subclasses on the basis of relatively minor differences in $C_H$ sequence and function, humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC), antibody-dependent cellular phagocytosis (ADCP), antibody-dependent neutrophil phagocytosis (ADNP), and antibody-dependent complement deposition (ADCD).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_{sub}H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567) after single cell sorting of an antigen specific B cell, an antigen specific plasmablast responding to an infection or immunization, or capture of linked heavy and light chains from single cells in a bulk sorted antigen specific collection. The "monoclonal antibodies" may also be isolated from phage antibody libraries using the techniques described in Clackson et al., Nature, 352:624-628 (1991) and Marks et al., J. Mol. Biol., 222: 581-597 (1991), for example.

A. General Methods

It will be understood that monoclonal antibodies will have several applications. These include the production of diagnostic kits for use in detecting and diagnosing cancer, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection or vaccination with a licensed or experimental vaccine. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants in animals include complete Freund's adjuvant (a non-specific stimulator of the immune response containing killed *Mycobacterium tuberculosis*), incomplete Freund's adjuvants and aluminum hydroxide adjuvant and in humans include alum, CpG, MFP59 and combinations of immunostimulatory molecules ("Adjuvant Systems", such as AS01 or AS03). Additional experimental forms of inoculation to induce AGR2-specific B cells is possible, including nanoparticle vaccines, or gene-encoded antigens delivered as DNA or RNA genes in a physical delivery system (such as lipid nanoparticle or on a gold biolistic bead), and delivered with needle, gene gun, transcutaneous electroporation device. The antigen gene also can be carried as encoded by a replication competent or defective viral vector such as adenovirus, adeno-associated virus, poxvirus, herpesvirus, or alphavirus replicon, or alternatively a virus like particle.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the mAb generating protocol. These cells may be obtained from biopsied spleens, lymph nodes, tonsils or adenoids, bone marrow aspirates or biopsies, tissue biopsies from mucosal organs like lung or GI tract, or from circulating blood. The antibody-producing B lymphocytes from the immunized animal or immune human are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984). HMMA2.5 cells or MFP-2 cells are particularly useful examples of such cells.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. In some cases, transformation of human B cells with Epstein Barr virus (EBV) as an initial step increases the size of the B cells, enhancing fusion with the relatively large-sized myeloma cells. Transformation efficiency by EBV is enhanced by using CpG and a Chk2 inhibitor drug in the transforming medium. Alternatively, human B cells can be activated by co-culture with transfected cell lines expressing CD40 Ligand (CD154) in medium containing additional soluble factors, such as IL-21 and human B cell Activating Factor (BAFF), a Type II member of the TNF superfamily. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986) and there are processes for better efficiency (Yu et al., 2008). Fusion procedures usually produce viable hybrids at low frequencies, about $1\times10^{-6}$ to $1\times10^{-8}$, but with optimized procedures one can achieve fusion efficiencies close to 1 in 200 (Yu et al., 2008). However, relatively low efficiency of fusion does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture medium. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides (HAT medium). Where azaserine is used, the medium is supplemented with hypoxanthine. Ouabain is added if the B cell source is an EBV-transformed human B cell line, in order to eliminate EBV-transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

mAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. Single B cells labelled with the antigen of interest can be sorted physically using paramagnetic bead selection or flow cytometric sorting, then RNA can be isolated from the single cells and antibody genes amplified by RT-PCR. Alternatively, antigen-specific bulk sorted populations of cells can be segregated into microvesicles and the matched heavy and light chain variable genes recovered from single cells using physical linkage of heavy and light chain amplicons, or common barcoding of heavy and light chain genes from a vesicle. Matched heavy and light chain genes form single cells also can be obtained from populations of antigen specific B cells by treating cells with cell-penetrating nanoparticles bearing RT-PCR primers and barcodes for marking transcripts with one barcode per cell. The antibody variable genes also can be isolated by RNA extraction of a hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately 104 times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. For example, the epitope to which a given antibody bind may consist of a single contiguous sequence of 3 or more (e.g., 3, 4, 5, 6, 7, 8, 9, 10, 11, 12, 13, 14, 15, 16, 17, 18, 19, 20) amino acids located within the antigen molecule (e.g., a linear epitope in a domain). Alternatively, the epitope may consist of a plurality of non-contiguous amino acids (or amino acid sequences) located within the antigen molecule (e.g., a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Cross-blocking can be measured in various binding assays such as ELISA, biolayer interferometry, or surface plasmon resonance. Other methods include alanine scanning mutational analysis, peptide blot analysis (Reineke (2004) Methods Mol. Biol. 248:443-63), peptide cleavage analysis, high-resolution electron microscopy techniques using single particle reconstruction, cryoEM, or tomography, crystallographic studies and NMR analysis. In addition, methods such as epitope excision, epitope extraction and chemical modification of antigens can be employed (Tomer (2000) Prot. Sci. 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267:252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the disclosure into groups of antibodies binding different epitopes.

The present disclosure includes antibodies that may bind to the same epitope, or a portion of the epitope. Likewise, the present disclosure also includes antibodies that compete for binding to a target or a fragment thereof with any of the specific exemplary antibodies described herein. One can easily determine whether an antibody binds to the same epitope as, or competes for binding with, a reference antibody by using routine methods known in the art. For example, to determine if a test antibody binds to the same epitope as a reference, the reference antibody is allowed to bind to target under saturating conditions. Next, the ability of a test antibody to bind to the target molecule is assessed. If the test antibody is able to bind to the target molecule following saturation binding with the reference antibody, it can be concluded that the test antibody binds to a different epitope than the reference antibody. On the other hand, if the test antibody is not able to bind to the target molecule following saturation binding with the reference antibody, then the test antibody may bind to the same epitope as the epitope bound by the reference antibody.

To determine if an antibody competes for binding with a reference anti-AGR2 antibody, the above-described binding methodology is performed in two orientations; In a first orientation, the reference antibody is allowed to bind to the AGR2 antigen under saturating conditions followed by assessment of binding of the test antibody to the AGR2 molecule. In a second orientation, the test antibody is allowed to bind to the AGR2 antigen molecule under saturating conditions followed by assessment of binding of the reference antibody to the AGR2 molecule. If, in both orientations, only the first (saturating) antibody is capable of binding to the AGR2, then it is concluded that the test antibody and the reference antibody compete for binding to the AGR2. As will be appreciated by a person of ordinary skill in the art, an antibody that competes for binding with a reference antibody may not necessarily bind to the identical epitope as the reference antibody but may sterically block binding of the reference antibody by binding an overlapping or adjacent epitope.

Two antibodies bind to the same or overlapping epitope if each competitively inhibits (blocks) binding of the other to the antigen. That is, a 1-, 5, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art. Structural studies with EM or crystallography also can demonstrate whether or not two antibodies that compete for binding recognize the same epitope.

In another aspect, there are provided monoclonal antibodies having clone-paired CDRs from the heavy and light chains as illustrated in Tables 3 and 4, respectively. Such antibodies may be produced by the clones discussed below in the Examples section using methods described herein.

In another aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table 1 and the amino acid sequences of Table 2.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins--Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogeny pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85:2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One particular example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example, with the parameters described herein, to determine percent sequence identity for the polynucleotides and polypeptides of the disclosure. Software for performing BLAST analyses is publicly available through the National Center for Biotechnology Information. The rearranged nature of an antibody sequence and the variable length of each gene requires multiple rounds of BLAST searches for a single antibody sequence. Also, manual assembly of different genes is difficult and error-prone. The sequence analysis tool IgBLAST (world-wide-web at ncbi.nlm.nih.gov/igblast/) identifies matches to the germline V, D and J genes, details at rearrangement junctions, the delineation of Ig V domain framework regions and complementarity determining regions. IgBLAST can analyze nucleotide or protein sequences and can process sequences in batches and allows searches against the germline gene databases and other sequence databases simultaneously to minimize the chance of missing possibly the best matching germline V gene.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

Yet another way of defining an antibody is as a "derivative" of any of the below-described antibodies and their antigen-binding fragments. The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, as variants having altered CH1, hinge, CH2, CH3 or CH4 regions, so as to form, for example, antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment, the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002), J. Biol. Chem. 277(30): 26733-26740; Davies J. et al. (2001), Biotechnology & Bioengineering 74(4): 288-294). Methods of altering carbohydrate contents are known to those skilled in the art, see, e.g., Wallick, S. C. et al. (1988), J. Exp. Med. 168(3): 1099-1109; Tao, M. H. et al.

(1989), J. Immunol. 143(8): 2595-2601; Routledge, E. G. et al. (1995), Transplantation 60(8):847-53; Elliott, S. et al. (2003), Nature Biotechnol. 21:414-21; Shields, R. L. et al. (2002), J. Biol. Chem. 277(30): 26733-26740).

A derivative antibody or antibody fragment can be generated with an engineered sequence or glycosylation state to confer preferred levels of activity in antibody dependent cellular cytotoxicity (ADCC), antibody-dependent cellular phagocytosis (ADCP), antibody-dependent neutrophil phagocytosis (ADNP), or antibody-dependent complement deposition (ADCD) functions as measured by bead-based or cell-based assays or in vivo studies in animal models.

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

C. Engineering of Antibody Sequences

In various embodiments, one may choose to engineer sequences of the identified antibodies for a variety of reasons, such as improved expression, improved cross-reactivity or diminished off-target binding. Modified antibodies may be made by any technique known to those of skill in the art, including expression through standard molecular biological techniques, or the chemical synthesis of polypeptides. Methods for recombinant expression are addressed elsewhere in this document. The following is a general discussion of relevant goals techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length IgG antibodies can be generated by subcloning heavy and light chain Fv DNAs from the cloning vector into an IgG plasmid vector, transfected into 293 (e.g., Freestyle) cells or CHO cells, and antibodies can be collected and purified from the 293 or CHO cell supernatant. Other appropriate host cells systems include bacteria, such as *E. coli*, insect cells (S2, Sf9, Sf29, High Five), plant cells (e.g., tobacco, with or without engineering for human-like glycans), algae, or in a variety of non-human transgenic contexts, such as mice, rats, goats or cows.

Expression of nucleic acids encoding antibodies, both for the purpose of subsequent antibody purification, and for immunization of a host, is also contemplated. Antibody coding sequences can be RNA, such as native RNA or modified RNA. Modified RNA contemplates certain chemical modifications that confer increased stability and low immunogenicity to mRNAs, thereby facilitating expression of therapeutically important proteins. For instance, N1-methyl-pseudouridine (N1 mΨ) outperforms several other nucleoside modifications and their combinations in terms of translation capacity. In addition to turning off the immune/eIF2α phosphorylation-dependent inhibition of translation, incorporated N1mΨ nucleotides dramatically alter the dynamics of the translation process by increasing ribosome pausing and density on the mRNA. Increased ribosome loading of modified mRNAs renders them more permissive for initiation by favoring either ribosome recycling on the same mRNA or de novo ribosome recruitment. Such modifications could be used to enhance antibody expression in vivo following inoculation with RNA. The RNA, whether native or modified, may be delivered as naked RNA or in a delivery vehicle, such as a lipid nanoparticle.

Alternatively, DNA encoding the antibody may be employed for the same purposes. The DNA is included in an expression cassette comprising a promoter active in the host cell for which it is designed. The expression cassette is advantageously included in a replicable vector, such as a conventional plasmid or minivector. Vectors include viral vectors, such as poxviruses, adenoviruses, herpesviruses, adeno-associated viruses, and lentiviruses are contemplated. Replicons encoding antibody genes such as alphavirus replicons based on VEE virus or Sindbis virus are also contemplated. Delivery of such vectors can be performed by needle through intramuscular, subcutaneous, or intradermal routes, or by transcutaneous electroporation when in vivo expression is desired.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), $F(ab')_2$) that are produced, for example, by the proteolytic cleavage of the mAbs, or single-chain immunoglobulins producible, for example, via recombinant means. F(ab') antibody derivatives are monovalent, while $F(ab')_2$ antibody derivatives are bivalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to IgG1 can increase antibody dependent cell cytotoxicity, switching to class A can improve tissue distribution, and switching to class M can improve valency.

Alternatively or additionally, it may be useful to combine amino acid modifications with one or more further amino acid modifications that alter C1q binding and/or the complement dependent cytotoxicity (CDC) function of the Fc region of an IL-23p19 binding molecule. The binding polypeptide of particular interest may be one that binds to C1q and displays complement dependent cytotoxicity. Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO/0042072, which is hereby incorporated by reference.

One can design an Fc region of an antibody with altered effector function, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of an antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

FcRn binding. Fc mutations can also be introduced and engineered to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, (J. Biol. Chem. 276:6591-6604). A number of methods are known that can result in increased half-life (Kuo and Aveson, (2011)), including amino acid modifications may be generated through techniques including alanine scanning mutagenesis, random mutagenesis and screening to assess the binding to the neonatal Fc receptor (FcRn) and/or the in vivo behavior. Computational strategies followed by mutagenesis may also be used to select one of amino acid mutations to mutate.

The present disclosure therefore provides a variant of an antigen binding protein with optimized binding to FcRn. In a particular embodiment, the said variant of an antigen binding protein comprises at least one amino acid modification in the Fc region of said antigen binding protein, wherein said modification is selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401 403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index in Kabat. In a further aspect of the disclosure the modifications are M252Y/S254T/T256E.

Additionally, various publications describe methods for obtaining physiologically active molecules whose half-lives are modified, see for example Kontermann (2009) either by introducing an FcRn-binding polypeptide into the molecules or by fusing the molecules with antibodies whose FcRn-binding affinities are preserved but affinities for other Fc receptors have been greatly reduced or fusing with FcRn binding domains of antibodies.

Derivatized antibodies may be used to alter the half-lives (e.g., serum half-lives) of parental antibodies in a mammal, particularly a human. Such alterations may result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present disclosure or fragments thereof in a mammal, preferably a human, results in a higher serum titer of said antibodies or antibody fragments in the mammal, and thus reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor.

Beltramello et al. (2010) previously reported the modification of neutralizing mAbs, due to their tendency to enhance dengue virus infection, by generating in which leucine residues at positions 1.3 and 1.2 of CH2 domain (according to the IMGT unique numbering for C-domain) were substituted with alanine residues. This modification, also known as "LALA" mutation, abolishes antibody binding to FcγRI, FcγRII and FcγRIIIa, as described by Hessell et al. (2007). The variant and unmodified recombinant mAbs were compared for their capacity to neutralize and enhance infection by the four dengue virus serotypes. LALA variants retained the same neutralizing activity as unmodified mAb but were completely devoid of enhancing activity. LALA mutations of this nature are therefore contemplated in the context of the presently disclosed antibodies.

Altered Glycosylation. A particular embodiment of the present disclosure is an isolated monoclonal antibody, or antigen binding fragment thereof, containing a substantially homogeneous glycan without sialic acid, galactose, or fucose. The monoclonal antibody comprises a heavy chain variable region and a light chain variable region, both of which may be attached to heavy chain or light chain constant regions respectively. The aforementioned substantially homogeneous glycan may be covalently attached to the heavy chain constant region.

Another embodiment of the present disclosure comprises a mAb with a novel Fc glycosylation pattern. The isolated monoclonal antibody, or antigen binding fragment thereof, is present in a substantially homogenous composition represented by the GNGN or G1/G2 glycoform. Fc glycosylation plays a significant role in anti-viral and anti-cancer properties of therapeutic mAbs. The disclosure is in line with a recent study that shows increased anti-lentivirus cell-mediated viral inhibition of a fucose free anti-HIV mAb in vitro. Elimination of core fucose dramatically improves the ADCC activity of mAbs mediated by natural killer (NK) cells but appears to have the opposite effect on the ADCC activity of polymorphonuclear cells (PMNs).

The isolated monoclonal antibody, or antigen binding fragment thereof, comprising a substantially homogenous composition represented by the GNGN or G1/G2 glycoform exhibits increased binding affinity for Fc gamma RI and Fc gamma RIII compared to the same antibody without the substantially homogeneous GNGN glycoform and with G0, G1F, G2F, GNF, GNGNF or GNGNFX containing glycoforms. In one embodiment of the present disclosure, the antibody dissociates from Fc gamma RI with a Kd of $1\times10^{-8}$ M or less and from Fc gamma RIII with a Kd of $1\times10^{-7}$ M or less.

Glycosylation of an Fc region is typically either N-linked or O-linked. N-linked refers to the attachment of the carbohydrate moiety to the side chain of an asparagine residue. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of an antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the antibody is expressed in cells that express beta (1,4)-N-acetylglucosaminyltransferase III (GnT III), such that GnT III adds GlcNAc to the IL-23p19 antibody. Methods for producing antibodies in such a fashion are provided in WO/9954342, WO/03011878, patent publication 20030003097A1, and Umana et al., Nature Biotechnology, 17:176-180, February 1999. Cell lines can be altered to enhance or reduce or eliminate certain post-translational modifications, such as glycosylation, using genome editing technology such as Clustered Regularly Interspaced Short Palindromic Repeats (CRISPR). For example, CRISPR technology can be used to eliminate genes encoding glycosylating enzymes in 293 or CHO cells used to express recombinant monoclonal antibodies.

Elimination of monoclonal antibody protein sequence liabilities. It is possible to engineer the antibody variable gene sequences obtained from human B cells to enhance their manufacturability and safety. Potential protein sequence liabilities can be identified by searching for sequence motifs associated with sites containing:

1) Unpaired Cys residues,
2) N-linked glycosylation,
3) Asn deamidation,
4) Asp isomerization,
5) SYE truncation,
6) Met oxidation,
7) Trp oxidation,
8) N-terminal glutamate,
9) Integrin binding,
10) CD11c/CD18 binding, or
11) Fragmentation Such motifs can be eliminated by altering the synthetic gene for the cDNA encoding recombinant antibodies.

Protein engineering efforts in the field of development of therapeutic antibodies clearly reveal that certain sequences or residues are associated with solubility differences (Fernandez-Escamilla et al., *Nature Biotech.*, 22 (10), 1302-1306, 2004; Chennamsetty et al., *PNAS*, 106 (29), 11937-11942, 2009; Voynov et al., *Biocon. Chem.*, 21 (2), 385-392, 2010) Evidence from solubility-altering mutations in the literature indicate that some hydrophilic residues such as aspartic acid, glutamic acid, and serine contribute significantly more favorably to protein solubility than other hydrophilic residues, such as asparagine, glutamine, threonine, lysine, and arginine.

Stability. Antibodies can be engineered for enhanced biophysical properties. One can use elevated temperature to unfold antibodies to determine relative stability, using average apparent melting temperatures. Differential Scanning calorimetry (DSC) measures the heat capacity, $C_p$, of a molecule (the heat required to warm it, per degree) as a function of temperature. One can use DSC to study the thermal stability of antibodies. DSC data for mAbs is particularly interesting because it sometimes resolves the unfolding of individual domains within the mAb structure, producing up to three peaks in the thermogram (from unfolding of the Fab, $C_H2$, and $C_H3$ domains). Typically unfolding of the Fab domain produces the strongest peak. The DSC profiles and relative stability of the Fc portion show characteristic differences for the human $IgG_1$, $IgG_2$, $IgG_3$, and $IgG_4$ subclasses (Garber and Demarest, *Biochem. Biophys. Res. Commun.* 355, 751-757, 2007). One also can determine average apparent melting temperature using circular dichroism (CD), performed with a CD spectrometer. Far-UV CD spectra will be measured for antibodies in the range of 200 to 260 nm at increments of 0.5 nm. The final spectra can be determined as averages of 20 accumulations. Residue ellipticity values can be calculated after background subtraction. Thermal unfolding of antibodies (0.1 mg/mL) can be monitored at 235 nm from 25-95° C. and a heating rate of 1° C./min. One can use dynamic light scattering (DLS) to assess for propensity for aggregation. DLS is used to characterize size of various particles including proteins. If the system is not disperse in size, the mean effective diameter of the particles can be determined. This measurement depends on the size of the particle core, the size of surface structures, and particle concentration. Since DLS essentially measures fluctuations in scattered light intensity due to particles, the diffusion coefficient of the particles can be determined. DLS software in commercial DLA instruments displays the particle population at different diameters. Stability studies can be done conveniently using DLS. DLS measurements of a sample can show whether the particles aggregate over time or with temperature variation by determining whether the hydrodynamic radius of the particle increases. If particles aggregate, one can see a larger population of particles with a larger radius. Stability depending on temperature can be analyzed by controlling the temperature in situ. Capillary electrophoresis (CE) techniques include proven methodologies for determining features of antibody stability. One can use an iCE approach to resolve antibody protein charge variants due to deamidation, C-terminal lysines, sialylation, oxidation, glycosylation, and any other change to the protein that can result in a change in pI of the protein. Each of the expressed antibody proteins can be evaluated by high throughput, free solution isoelectric focusing (IEF) in a capillary column (cIEF), using a Protein Simple Maurice instrument. Whole-column UV absorption detection can be performed every 30 seconds for real time monitoring of molecules focusing at the isoelectric points (pIs). This approach combines the high resolution of traditional gel IEF with the advantages of quantitation and automation found in column-based separations while eliminating the need for a mobilization step. The technique yields reproducible, quantitative analysis of identity, purity, and heterogeneity profiles for the expressed antibodies. The results identify charge heterogeneity and molecular sizing on the antibodies, with both absorbance and native fluorescence detection modes and with sensitivity of detection down to 0.7 μg/mL.

Solubility. One can determine the intrinsic solubility score of antibody sequences. The intrinsic solubility scores can be calculated using CamSol Intrinsic (Sormanni et al., *J Mol Biol* 427, 478-490, 2015). The amino acid sequences for residues 95-102 (Kabat numbering) in HCDR3 of each antibody fragment such as a scFv can be evaluated via the online program to calculate the solubility scores. One also can determine solubility using laboratory techniques. Various techniques exist, including addition of lyophilized protein to a solution until the solution becomes saturated and the solubility limit is reached, or concentration by ultrafiltration in a microconcentrator with a suitable molecular weight cut-off. The most straightforward method is induction of amorphous precipitation, which measures protein solubility using a method involving protein precipitation using ammonium sulfate (Trevino et al., *J Mol Biol,* 366:449-460, 2007). Ammonium sulfate precipitation gives quick and accurate information on relative solubility values. Ammonium sulfate precipitation produces precipitated solutions with well-defined aqueous and solid phases and requires relatively small amounts of protein. Solubility measurements performed using induction of amorphous precipitation by ammonium sulfate also can be done easily at different pH values. Protein solubility is highly pH dependent, and pH is considered the most important extrinsic factor that affects solubility.

Autoreactivity. Generally, it is thought that autoreactive clones should be eliminated during ontogeny by negative selection, however it has become clear that many human naturally occurring antibodies with autoreactive properties persist in adult mature repertoires, and the autoreactivity may enhance the antiviral function of many antibodies to pathogens. It has been noted that HCDR3 loops in antibodies during early B cell development are often rich in positive charge and exhibit autoreactive patterns (Wardemann et al., *Science* 301, 1374-1377, 2003). One can test a given antibody for autoreactivity by assessing the level of binding to human origin cells in microscopy (using adherent HeLa or HEp-2 epithelial cells) and flow cytometric cell surface staining (using suspension Jurkat T cells and 293S human embryonic kidney cells). Autoreactivity also can be surveyed using assessment of binding to tissues in tissue arrays.

Preferred residues ("Human Likeness"). B cell repertoire deep sequencing of human B cells from blood donors is being performed on a wide scale in many recent studies. Sequence information about a significant portion of the human antibody repertoire facilitates statistical assessment of antibody sequence features common in healthy humans. With knowledge about the antibody sequence features in a human recombined antibody variable gene reference database, the position specific degree of "Human Likeness" (HL) of an antibody sequence can be estimated. HL has been shown to be useful for the development of antibodies in clinical use, like therapeutic antibodies or antibodies as vaccines. The goal is to increase the human likeness of antibodies to reduce potential adverse effects and anti-antibody immune responses that will lead to significantly decreased efficacy of the antibody drug or can induce serious health implications. One can assess antibody characteristics of the combined antibody repertoire of three healthy human blood donors of about 400 million sequences in total and created a novel "relative Human Likeness" (rHL) score that focuses on the hypervariable region of the antibody. The rHL score allows one to easily distinguish between human (positive score) and non-human sequences (negative score).

Antibodies can be engineered to eliminate residues that are not common in human repertoires.

D. Single Chain Antibody Variable Fragments

A single chain variable fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma or B cell. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5\times10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Multispecific Antibodies

In certain embodiments, antibodies of the present disclosure are bispecific or multispecific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an anti-pathogen arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and Fc gamma RIII (CD16), so as to focus and localize cellular defense mechanisms to the infected cell. Bispecific antibodies may also be used to localize cytotoxic agents to infected cells. These antibodies possess a pathogen-binding arm and an arm that binds the cytotoxic agent (e.g., saporin, anti-interferon-a, *vinca* alkaloid, ricin A chain, methotrexate or radioactive isotope hapten). Bispecific antibodies can be prepared as full-length antibodies or antibody fragments (e.g., $F(ab')_2$ bispecific antibodies). WO 96/16673 describes a bispecific anti-ErbB2/anti-Fc gamma RIII antibody and U.S. Pat. No. 5,837,234 discloses a bispecific anti-ErbB2/anti-Fc gamma RI antibody. A bispecific anti-ErbB2/Fc alpha antibody is shown in WO98/02463. U.S. Pat. No. 5,821,337 teaches a bispecific anti-ErbB2/anti-CD3 antibody.

Methods for making bispecific antibodies are known in the art. Traditional production of full-length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable regions with the desired binding specificities (antibody-antigen combining sites) are fused to immunoglobulin constant domain sequences. Preferably, the fusion is with an Ig heavy chain constant domain, comprising at least part of the hinge, $C_{H2}$, and $C_{H3}$ regions. It is preferred to have the first heavy-chain constant region ($C_{H1}$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

In a particular embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the CH3 domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229:81 (1985) describe a procedure wherein intact antibodies are proteolytically cleaved to generate $F(ab')_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Techniques exist that facilitate the direct recovery of Fab'-SH fragments from *E. coli*, which can be chemically coupled to form bispecific antibodies. Shalaby et al., J. Exp. Med., 175:217-225 (1992) describe the production of a humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described (Merchant et al., *Nat. Biotechnol.* 16, 677-681 (1998). doi:10.1038/nbt0798-677pmid: 9661204). For example, bispecific antibodies have been produced using leucine zippers (Kostelny et al., J. Immunol., 148(5):1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

In a particular embodiment, a bispecific or multispecific antibody may be formed as a DOCK-AND-LOCK™ (DNL™) complex (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of CAMP-dependent protein kinase (PKA) and an anchor domain (AD) sequence derived from any of a variety of AKAP proteins (Baillie et al., *FEBS Letters.* 2005; 579:3264; Wong and Scott, *Nat. Rev. Mol. Cell Biol.* 2004; 5:959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Antibodies with more than two valencies are contemplated. For example, trispecific antibodies can be prepared (Tutt et al., J. Immunol. 147:60, 1991; Xu et al., *Science,* 358(6359):85-90, 2017). A multivalent antibody may be internalized (and/or catabolized) faster than a bivalent antibody by a cell expressing an antigen to which the antibodies bind. The antibodies of the present disclosure can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable regions. For instance, the polypeptide chain(s) may comprise VD1-$(X1)_n$-VD2-$(X2)_n$-Fc, wherein VD1 is a first variable region, VD2 is a second variable region, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable region polypeptides. The multivalent antibody herein may, for instance, comprise from about two to about eight light chain variable region polypeptides. The light chain variable region polypeptides contemplated here comprise a light chain variable region and, optionally, further comprise a $C_L$ domain.

Charge modifications are particularly useful in the context of a multispecific antibody, where amino acid substitutions in Fab molecules result in reducing the mispairing of light chains with non-matching heavy chains (Bence-Jones-type side products), which can occur in the production of Fab-based bi-/multispecific antigen binding molecules with a VH/VL exchange in one (or more, in case of molecules comprising more than two antigen-binding Fab molecules) of their binding arms (see also PCT publication no. WO 2015/150447, particularly the examples therein, incorporated herein by reference in its entirety).

Accordingly, in particular embodiments, an antibody comprised in the therapeutic agent comprises (a) a first Fab molecule which specifically binds to a first antigen (b) a second Fab molecule which specifically binds to a second antigen, and wherein the variable domains VL and VH of the Fab light chain and the Fab heavy chain are replaced by each other, wherein the first antigen is an activating T cell antigen and the second antigen is a target cell antigen, or the first antigen is a target cell antigen and the second antigen is an activating T cell antigen; and wherein i) in the constant domain CL of the first Fab molecule under a) the amino acid at position 124 is substituted by a positively charged amino acid (numbering according to Kabat), and wherein in the constant domain CH1 of the first Fab molecule under a) the amino acid at position 147 or the amino acid at position 213 is substituted by a negatively charged amino acid (numbering according to Kabat EU index); or ii) in the constant domain CL of the second Fab molecule under b) the amino acid at position 124 is substituted by a positively charged amino acid (numbering according to Kabat), and wherein in the constant domain CH1 of the second Fab molecule under b) the amino acid at position 147 or the amino acid at position 213 is substituted by a negatively charged amino acid (numbering according to Kabat EU index).

The antibody may not comprise both modifications mentioned under i) and ii). The constant domains CL and CH1 of the second Fab molecule are not replaced by each other (i.e., remain unexchanged).

In another embodiment of the antibody, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 or the amino acid at position 213 is substituted independently by glutamic acid (E), or aspartic acid (D) (numbering according to Kabat EU index).

In a further embodiment, in the constant domain CL of the first Fab molecule under a) the amino acid at position 124 is substituted independently by lysine (K), arginine (R) or histidine (H) (numbering according to Kabat), and in the constant domain CH1 of the first Fab molecule under a) the amino acid at position 147 is substituted independently by glutamic acid (E), or aspartic acid (D) (numbering according to Kabat EU index).

In a particular embodiment, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first Fab molecule under a) the amino acid at position 124 is substituted by lysine (K) (numbering according to Kabat) and the amino acid at position 123 is substituted by lysine (K) or arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first Fab molecule under a) the amino acid at position 124 is substituted by lysine (K) (numbering according to Kabat) and the amino acid at position 123 is substituted by arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

F. Chimeric Antigen Receptors

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell, with transfer of their coding sequence facilitated by retroviral vectors. In this way, a large number of target-specific T cells can be generated for adoptive cell transfer. Phase I clinical studies of this approach show efficacy.

The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g., neuroblastoma cells). To target malignant B cells, investigators have redirected the specificity of T cells using a chimeric immunoreceptor specific for the B-lineage molecule, CD19.

The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows to the scFv to orient in different directions to enable antigen binding. The transmembrane domain is a typical hydrophobic alpha helix usually derived from the original molecule of the signaling endodomain which protrudes into the cell and transmits the desired signal.

Type I proteins are in fact two protein domains linked by a transmembrane alpha helix in between. The cell membrane lipid bilayer, through which the transmembrane domain passes, acts to isolate the inside portion (endodomain) from the external portion (ectodomain). It is not so surprising that attaching an ectodomain from one protein to an endodomain of another protein results in a molecule that combines the recognition of the former to the signal of the latter.

Ectodomain. A signal peptide directs the nascent protein into the endoplasmic reticulum. This is essential if the receptor is to be glycosylated and anchored in the cell membrane. Any eukaryotic signal peptide sequence usually works fine. Generally, the signal peptide natively attached to the amino-terminal most component is used (e.g., in a scFv with orientation light chain-linker-heavy chain, the native signal of the light-chain is used The antigen recognition domain is usually an scFv. There are however many alternatives. An antigen recognition domain from native T-cell receptor (TCR) alpha and beta single chains have been described, as have simple ectodomains (e.g., CD4 ectodomain to recognize HIV infected cells) and more exotic recognition components such as a linked cytokine (which leads to recognition of cells bearing the cytokine receptor). In fact, almost anything that binds a given target with high affinity can be used as an antigen recognition region.

A spacer region links the antigen binding domain to the transmembrane domain. It should be flexible enough to allow the antigen binding domain to orient in different directions to facilitate antigen recognition. The simplest form is the hinge region from IgG1. Alternatives include the CH2CH3 region of immunoglobulin and portions of CD3. For most scFv based constructs, the IgG1 hinge suffices. However, the best spacer often has to be determined empirically.

Transmembrane domain. The transmembrane domain is a hydrophobic alpha helix that spans the membrane. Generally, the transmembrane domain from the most membrane proximal component of the endodomain is used. Interestingly, using the CD3-zeta transmembrane domain may result in incorporation of the artificial TCR into the native TCR a factor that is dependent on the presence of the native CD3-zeta transmembrane charged aspartic acid residue. Different transmembrane domains result in different receptor stability. The CD28 transmembrane domain results in a brightly expressed, stable receptor.

Endodomain. This is the "business-end" of the receptor. After antigen recognition, receptors cluster and a signal is transmitted to the cell. The most commonly used endodomain component is CD3-zeta which contains 3 ITAMs. This transmits an activation signal to the T cell after antigen is bound. CD3-zeta may not provide a fully competent activation signal and additional co-stimulatory signaling is needed.

"First-generation" CARs typically had the intracellular domain from the CD3 &-chain, which is the primary transmitter of signals from endogenous TCRs. "Second-generation" CARs add intracellular signaling domains from various costimulatory protein receptors (e.g., CD28, 41BB, ICOS) to the cytoplasmic tail of the CAR to provide additional signals to the T cell. Preclinical studies have indicated that the second generation of CAR designs improves the antitumor activity of T cells. More recent, "third-generation" CARs combine multiple signaling domains, such as CD3z-CD28-41BB or CD3z-CD28-OX40, to further augment potency.

G. ADCs

Antibody Drug Conjugates or ADCs are a new class of highly potent biopharmaceutical drugs designed as a targeted therapy for the treatment of people with infectious disease. ADCs are complex molecules composed of an antibody (a whole mAb or an antibody fragment such as a single-chain variable fragment, or scFv) linked, via a stable chemical linker with labile bonds, to a biological active cytotoxic/anti-viral payload or drug. Antibody Drug Conjugates are examples of bioconjugates and immunoconjugates.

By combining the unique targeting capabilities of monoclonal antibodies with the cancer-killing ability of cytotoxic drugs, antibody-drug conjugates allow sensitive discrimination between healthy and diseased tissue. This means that, in contrast to traditional systemic approaches, antibody-drug conjugates target and attack the infected cell so that healthy cells are less severely affected.

In the development ADC-based anti-tumor therapies, an anticancer drug (e.g., a cell toxin or cytotoxin) is coupled to an antibody that specifically targets a certain cell marker (e.g., a protein that, ideally, is only to be found in or on infected cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cell or impairs viral replication. Due to this targeting, ideally the drug has lower side effects and gives a wider therapeutic window than other agents.

A stable link between the antibody and cytotoxic/anti-viral agent is a crucial aspect of an ADC. Linkers are based on chemical motifs including disulfides, hydrazones or peptides (cleavable), or thioethers (noncleavable) and control the distribution and delivery of the cytotoxic agent to the target cell. Cleavable and noncleavable types of linkers have been proven to be safe in preclinical and clinical trials. Brentuximab vedotin includes an enzyme-sensitive cleavable linker that delivers the potent and highly toxic antimicrotubule agent Monomethyl auristatin E or MMAE, a synthetic antineoplastic agent, to human specific CD30-positive malignant cells. Because of its high toxicity MMAE, which inhibits cell division by blocking the polymerization of tubulin, cannot be used as a single-agent chemotherapeutic drug. However, the combination of MMAE linked to an anti-CD30 monoclonal antibody (cAC10, a cell membrane protein of the tumor necrosis factor or TNF receptor) proved to be stable in extracellular fluid, cleavable by cathepsin and safe for therapy. Trastuzumab emtansine, the other approved ADC, is a combination of the microtubule-formation inhibitor mertansine (DM-1), a derivative of the Maytansine, and antibody trastuzumab (Herceptin®/Genentech/Roche) attached by a stable, non-cleavable linker.

The availability of better and more stable linkers has changed the function of the chemical bond. The type of linker, cleavable or noncleavable, lends specific properties to the cytotoxic (anti-cancer) drug. For example, a non-cleavable linker keeps the drug within the cell. As a result, the entire antibody, linker and cytotoxic agent enter the targeted cancer cell where the antibody is degraded to the level of an amino acid. The resulting complex—amino acid, linker and cytotoxic agent—now becomes the active drug. In contrast, cleavable linkers are catalyzed by enzymes in the host cell where it releases the cytotoxic agent.

Another type of cleavable linker, currently in development, adds an extra molecule between the cytotoxic/anti-viral drug and the cleavage site. This linker technology allows researchers to create ADCs with more flexibility without worrying about changing cleavage kinetics. Researchers are also developing a new method of peptide cleavage based on Edman degradation, a method of sequencing amino acids in a peptide. Future direction in the development of ADCs also include the development of site-specific conjugation (TDCs) to further improve stability and therapeutic index and a emitting immunoconjugates and antibody-conjugated nanoparticles.

H. BiTES

Bi-specific T-cell engagers (BiTEs) are a class of artificial bispecific monoclonal antibodies that are investigated for the use as anti-cancer drugs. They direct a host's immune system, more specifically the T cells' cytotoxic activity, against infected cells. BiTE is a registered trademark of Micromet AG.

BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to an infected cell via a specific molecule.

Like other bispecific antibodies, and unlike ordinary monoclonal antibodies, BiTEs form a link between T cells and target cells. This causes T cells to exert cytotoxic/anti-viral activity on infected cells by producing proteins like perforin and granzymes, independently of the presence of MHC I or co-stimulatory molecules. These proteins enter infected cells and initiate the cell's apoptosis. This action mimics physiological processes observed during T cell attacks against infected cells.

I. INTRABODIES

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

J. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. TREATMENT/PREVENTION OF CANCERS

A. Formulation and Administration

The present disclosure provides pharmaceutical compositions comprising anti-AGR2 antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, intrarectal, vaginal, topical or delivered by mechanical ventilation.

Vaccines can be formulated for parenteral administration, e.g., formulated for injection via the intradermal, intravenous, intramuscular, subcutaneous, or even intraperitoneal routes. The vaccine could alternatively be administered by a topical route directly to the mucosa, for example, by nasal drops, inhalation, by nebulizer, or via intrarectal or vaginal delivery. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

B. ADCC

Antibody-dependent cell-mediated cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. By "antibody having increased/reduced antibody dependent cell-mediated cytotoxicity (ADCC)" is meant an antibody having increased/reduced ADCC as determined by any suitable method known to those of ordinary skill in the art.

As used herein, the term "increased/reduced ADCC" is defined as either an increase/reduction in the number of target cells that are lysed in a given time, at a given concentration of antibody in the medium surrounding the target cells, by the mechanism of ADCC defined above, and/or a reduction/increase in the concentration of antibody, in the medium surrounding the target cells, required to achieve the lysis of a given number of target cells in a given time, by the mechanism of ADCC. The increase/reduction in ADCC is relative to the ADCC mediated by the same antibody produced by the same type of host cells, using the same standard production, purification, formulation and storage methods (which are known to those skilled in the art), but that has not been engineered. For example, the increase in ADCC mediated by an antibody produced by host cells engineered to have an altered pattern of glycosylation (e.g., to express the glycosyltransferase, GnTIII, or other glycosyltransferases) by the methods described herein, is relative to the ADCC mediated by the same antibody produced by the same type of non-engineered host cells.

C. CDC

Complement-dependent cytotoxicity (CDC) is a function of the complement system. It is the processes in the immune system that kill pathogens by damaging their membranes without the involvement of antibodies or cells of the immune system. There are three main processes. All three insert one or more membrane attack complexes (MAC) into the pathogen which cause lethal colloid-osmotic swelling, i.e., CDC. It is one of the mechanisms by which antibodies or antibody fragments have an anti-viral effect.

D. Cancers

While hyperproliferative diseases can be associated with any disease which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. In some embodiments, the molecules described herein may be used to treat cancer, decreased cancer cell burden, decrease tumor size, limit or prevent metastasis and/or overcome drug resistance in a variety of cancers or other malignancies.

In some embodiments, cancer, cancer tissue, or cancer cells may be treated by the methods and compositions disclosed herein. In some embodiments, cancer cells or tissue that may be treated include but are not limited to cells or tissue from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In some embodiments, the cancer that may be treated may be of the following histological types: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia, including hairy cell leukemia; chronic lymphocytic leukemia (CLL); acute lymphoblastic leukemia (ALL); acute myeloid leukemia (AML); and chronic myeloblastic leukemia.

In another aspect, the compositions and methods disclosed herein may be used to treat cancer or other hyperproliferative diseases. While hyperproliferative diseases can be associated with any disease which causes a cell to begin to reproduce uncontrollably, the prototypical example is cancer. One of the elements of cancer is that the cell's normal apoptotic cycle is interrupted. As such, agents that interrupt the growth of the cells are important as therapeutic agents for treating these diseases. In this disclosure, the compounds of the present disclosure thereof may be used to lead to decreased cell counts and may be used to treat a variety of types of cancer.

In some embodiments, cancer cells that may be treated with the compositions of the present disclosure include, but are not limited to, bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, and uterus cells.

In some embodiments, tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

In certain embodiments regarding methods of treating cancer in a patient comprise administering to the patient a pharmaceutically effective amount of a molecule of the present disclosure, for example where the pharmaceutically effective amount is 0.001-1000 mg/kg. In certain embodiments, the pharmaceutically effective amount is administered in a single dose per day. In certain embodiments, the pharmaceutically effective amount is administered in two or more doses per day. The compound may be administered by contacting a tumor cell during ex vivo purging, for example. The method of treatment may comprise any one or more of the following: a) inducing cytotoxicity in a tumor cell; b) killing a tumor cell; c) inducing apoptosis in a tumor cell; d) inducing differentiation in a tumor cell; or e) inhibiting growth in a tumor cell. The tumor cell may be any type of tumor cell, such as a brain cell. Other types of cells include, for example, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or a soft tissue cancer cell.

In some embodiments, treatment methods further comprise monitoring treatment progress. In some of these embodiments, the method includes the step of determining a level of changes in hematological parameters and/or cancer stem cell (CSC) analysis with cell surface proteins as diagnostic markers or diagnostic measurement (e.g., screen, assay) in a patient suffering from or susceptible to a disorder or symptoms thereof associated with cancer in which the patient has been administered a therapeutic amount of a compound or composition as described herein. The level of the marker determined in the method can be compared to known levels of marker in either healthy normal controls or in other afflicted patients to establish the patient's disease status. In some embodiments, a second level of the marker in the patient is determined at a time point later than the determination of the first level, and the two levels are compared to monitor the course of disease or the efficacy of the therapy. In some embodiments, a pre-treatment level of marker in the patient is determined prior to beginning treatment according to the methods described herein; this pre-treatment level of marker can then be compared to the level of marker in the patient after the treatment commences, to determine the efficacy of the treatment.

In some embodiments, the patient is a mammal, e.g., a primate, preferably a higher primate, e.g., a human (e.g., a patient having, or at risk of having, a disorder described herein). In some embodiments, the patient is in need of enhancing the patient's immune response. In certain embodiments, the patient is, or is at risk of being, immunocompromised. For example, in some embodiments, the patient is undergoing or has undergone a chemotherapeutic treatment and/or radiation therapy. Alternatively, or in combination, the patient is, or is at risk of being, immunocompromised as a result of an infection.

IV. Antibody Conjugates

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Additional types of antibodies contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939, 350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl) propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. IMMUNODETECTION METHODS

In still further embodiments, the present disclosure concerns immunodetection methods for binding, purifying, removing, quantifying and otherwise generally detecting AGR2-expressing cancer cells. While such methods can be applied in a traditional sense, another use will be in quality control and monitoring of vaccine stocks, where antibodies according to the present disclosure can be used to assess the amount or integrity (i.e., long term stability) of antigens in samples. Alternatively, the methods may be used to screen various antibodies for appropriate/desired reactivity profiles.

Other immunodetection methods include specific assays for determining the presence of AGR2 in a subject. A wide variety of assay formats are contemplated, but specifically those that would be used to detect AGR2-expressing or over-expressing cancer cells in a fluid obtained from a subject, such as saliva, blood, plasma, sputum, semen or urine. The assays may be advantageously formatted for non-healthcare (home) use, including lateral flow assays (see below) analogous to home pregnancy tests. These assays may be packaged in the form of a kit with appropriate reagents and instructions to permit use by the subject of a family member.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation is contemplated. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing the garget, and contacting the sample with a first antibody in accordance with the present disclosure, as the case may be, under conditions effective to allow the formation of immunocomplexes.

These methods include methods for purifying cancer cells or related antigens from a sample. The antibody will preferably be linked to a solid support, such as in the form of a column matrix, and the sample suspected of containing the cancer cells or antigenic component will be applied to the immobilized antibody. The unwanted components will be washed from the column, leaving the cancer cell immunocomplexed to the immobilized antibody, which is then collected by removing the organism or antigen from the column.

The immunobinding methods also include methods for detecting and quantifying the amount of cancer cell or related components in a sample and the detection and quantification of any immune complexes formed during the binding process. Here, one would obtain a sample suspected of containing cancer cell or its antigens and contact the sample with an antibody that binds cancer cells or components thereof, followed by detecting and quantifying the amount of immune complexes formed under the specific conditions. In terms of antigen detection, the biological sample analyzed may be any sample that is suspected of containing cancer cells or AGR2 antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to cancer cells or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, for example, with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings. Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

VI. KITS

In still further embodiments, the present disclosure concerns immunodetection kits for use with the immunodetection methods described above. As the antibodies are included in the kit, optionally with AGR2. The immunodetection kits will thus comprise, in suitable container means, a first antibody that binds to AGR2, and optionally an immunodetection reagent.

In certain embodiments, the AGR2 antibody may be pre-bound to a solid support, such as a column matrix and/or well of a microtiter plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

As mentioned above, kits may further comprise a suitably aliquoted composition of the AGR2, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

VII. EXAMPLES

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Discovery of anti-AGR2 scFv clones. The inventors confirmed that AGR2 is overexpressed in epithelial and stromal compartments of PDAC tumors but not normal pancreatic ductal cells or islet cell carcinoma, suggesting a unique expression pattern of AGR2 in PDAC. They also showed that in addition to intracellular expression, AGR2 was secreted from the cell where it localized to the cell surface and was released into the conditioned media of PDAC cells. The inventors hypothesized that AGR2 could be targeted with immunotherapies to cause T cell activation within the PDAC TME to generate an anti-tumor immune response.

To pursue this hypothesis, the inventors used phage display technology to identify multiple AGR2 specific scFv. Initial screening of monoclonal phage and soluble scFv from crude bacterial lysates confirmed AGR2 specific binding of four scFv. The scFvs were cloned into the bacterial expression vector pET22b amd produced and purified them in BL21(DE3) *E. coli*. A comparison of the four AGR2-specific scFv revealed that clone-15 had the greatest binding specificity and affinity for AGR2 by ELISA and SPR, with a KD of 179.5 nM (4.692 μg/ml, FIG. 1A). AGR2-scFv-15 also exhibited the best thermodynamic stability with a melting temperature of 78° C. (FIG. 1B).

AG2R2xCD3 BiTE construction and expression. The inventors next constructed an AGR2xCD3 BiTE that they reasoned would simultaneously engage AGR2 in the PDAC TME and CD3 on T cells to activate T cells and drive an anti-tumor immune response. The BiTE was designed using a similar scaffold to that of blinatumomab, which is FDA approved for the treatment of B cell ALL. A tandem scFv format was used, linking the anti-AGR2 scFv clone-15 to an anti-CD3 scFv derived from the sequence of Orthoclone OKT3. OKT3 is a high affinity agonistic CD3 antibody that stimulates TCR signaling, induces T cell activation, and is commonly used in the construction of bispecific T cell engagers. Methods were optimized to produce and purify the BiTE from *E. coli*. The identity purity of purification products was confirmed by SDS-PAGE, AGR2 binding functionality was confirmed by ELISA (FIG. 2A), and CD3 binding was confirmed by flow cytometry using human CD3+ Jurkat T cells (FIG. 2B). One of the challenges we foresaw was that OKT3 is specific for human CD3 but has minimal affinity for mouse CD3, which shares <60% homology with human CD3 isoforms at the amino acid level.[46] Thus, while the OKT3 BiTE, while befitting for a human therapeutic, has limited utility in preclinical validation experiments using syngeneic mouse models. To address this, the inventors also created a mouse specific BiTE (mCD3xAGR2) using the murine specific agonistic anti-CD3 scFv clone 145-2C11. As with the human BiTE, we confirmed binding to AGR2 in ELISA assays and binding to mouse EL4 T cells (FIG. 2C-D).

AGR2xCD3 BiTE induces T cell dependent killing of AGR2+ PDAC cells. The inventors next evaluated the functionality of our AGR2xCD3 BiTE construct in T cell dependent cellular cytotoxicity (TDCC) assays. They used AGR2 expressing Capan1 cells co-cultured with human naïve PBMCs at an effector:tumor (E:T) ratio of 10:1. At the end of the incubation period, non-adherent immune cells were removed by aspiration leaving the adherent PDAC cells, and viability was measured using the Cell TiterGlo assay system. The addition of the AGR2xCD3 BiTE induced significant T cell activation in PBMCs cultures when Capan1 cells were present as indicated by the production of IFN gamma (FIG. 3A). Importantly, the addition of the BiTE dramatically induced the death of Capan1 cells in a T cell dependent manner (FIG. 3B). For example, the $EC_{50}$ of the BiTE was 30 nM compared to 19,830 nM and 16,460 nM for scFv clone-15 and the BiTE alone (no PBMCs), respectively.

In summary, the inventors have successfully created human and mouse AGR2xCD3 BiTEs and demonstrated that it is capable of inducing TDCC in an in vitro PDAC cell model overexpressing AGR2.

TABLE 1

NUCLEOTIDE SEQUENCES FOR ScFv

| Clone | SEQ ID NO: | Variable Sequence Region |
|---|---|---|
| 1 | 1 | GAGGTGCAGCTGTTGGAGTCTGGGGGAGGCTTGGTACAGCCTGGGGGGTCCCTGAGACTCTCCT<br>GTGCAGCCTCTGGATTCACCTTTAGCAGCTATGCCATGAGCTGGGTCCGCCAGGCTCCAGGGAA<br>GGGGCTGGAGTGGGTCTCAGGTATTTAGAGTACGGGTGCGTTGACAGCTTACGCAGACTCCGTG<br>AAGGGCCGGTTCACCATCTCCAGAGACAATTCCAAGAACACGCTGTATCTGCAAATGAACAGCCT<br>GAGAGCCGAGGACACGGCCGTATATTACTGTGCGAAATTGGCTTAGACGTTTGACTACTGGGGCC<br>AGGGAACCCTGGTCACCGTCTCGAGCGGTGGAGGCGGTTCAGGCGGAGGTGGCAGCGGCGGTG<br>GCGGGTCGACGGACATCCAGATGACCCAGTCTCCATCTTCCCTGTCTGCATCTGTAGGAGACAGA<br>GTCACCATCACTTGCCGGGCAAGTCAGAGCATTAGCAGCTATTTAAATTGGTATCAGCAGAAACCA<br>GGGAAAGCCCCTAAGCTCCTGATCTATCGGGCATCCTCCTTGCAAAGTGGGGTCCCATCAAGGTT |

TABLE 1-continued

| NUCLEOTIDE SEQUENCES FOR ScFv | | |
|---|---|---|
| Clone | SEQ ID NO: | Variable Sequence Region |
| | | CAGTGGCAGTGGATCTGGGACAGATTTCACTCTCACCATCAGCAGTCTGCAACCTGAAGATTTTGC<br>AACTTACTACTGTCAACAGACTCGGAGGCTGCCTGTGACGTTCGGCCAAGGGACCAAGGTGGAAA<br>TCAAA |
| 15 | 2 | GAGGTGCAGCTGTTGGAGTCTGGGGGAGGCTTGGTACAGCCTGGGGGGTCCCTGAGACTCTCCT<br>GTGCAGCCTCTGGATTCACCTTTAGCAGCTATGCCATGAGCTGGGTCCGCCAGGCTCCAGGGAA<br>GGGGCTGGAGTGGGTCTCAGGTATTTCTGCTCAGGGTGCGCATACAACGTACGCAGACTCCGTG<br>AAGGGCAGGTTCACCATCTCCAGAGACAATTCCAAGAACACGCTGTATCTGCAAATGAACAGCCT<br>GAGAGCCGAGGACACGGCCGTATATTACTGTGCGAAAACGTATAAGGGGTTTGACTACTGGGGCC<br>AGGGAACCCTGGTCACCGTCTCGAGCGGTGGAGGCGGTTCAGGCGGAGGTGGCAGCGGCGGTG<br>GCGGGTCGACGGACATCCAGATGACCCAGTCTCCATCCTCCCTGTCTGCATCTGTAGGAGACAGA<br>GTCACCATCACTTGCCGGGCAAGTCAGAGCATTAGCAGCTATTTAAATTGGTATCAGCAGAAACCA<br>GGGAAAGCCCCTAAGCTCCTGATCTATAGTGCATCCAGGTTGCAAAGTGGGGTCCCATCAAGGTT<br>CAGTGGCAGTGGATCTGGGACAGATTTCACTCTCACCATCAGCAGTCTGCAACCTGAAGATTTTGC<br>AACTTACTACTGTCAACAGGGGCGGCGGATGCCTCCGACGTTCGGCCAAGGGACCAAGGTGGAA<br>ATCAAA |
| 19 | 3 | CGAGGTGCAGCTGTTGGAGTCTGGGGGAGGCTTGGTACAGCCTGGGGGGTCCTGAGACTCTCCT<br>GTGCAGCCTCTGGATTCACCTTTAGCAGCTATGCCATGAGCTGGGTCCGCCAGGCTCCAGGGAA<br>GGGGCTGGAGTGGGTCTCAGCGATTGCGTCGTAGGGTGTGGCTACAGGGTACGCAGACTCCGTG<br>AAGGGCCGGTTCACCATCTCCAGAGACAATTCCAAGAACACGCTGTATCTGCAAATGAACAGCCT<br>GAGAGCCGAGGACACGGCCGTATATTACTGTGCGAAATTGGATCAGCATTTTGACTACTGGGGCC<br>AGGGAACCCTGGTCACCGTCTCGAGCGGTGGAGGCGGTTCAGGCGGAGGTGGCAGCGGCGGTG<br>GCGGGTCGACGGACATCCAGATGACCCAGTCTCCATCCTCCCTGTCTGCATCTGTAGGAGACAGA<br>GTCACCATCACTTGCCGGGCAAGTCAGAGCATTAGCAGCTATTTAAATTGGTATCAGCAGAAACCA<br>GGGAAAGCCCCTAAGCTCCTGATCTATCAGGCATCCCGGTTGCAAAGTGGGGTCCCATCAAGGTT<br>CAGTGGCAGTGGATCTGGGACAGATTTCACTCTCACCATCAGCAGTCTGCAACCTGAAGATTTTGC<br>AACTTACTACTGTCAACAGGCGAGGCGTCTGCCTCTTACGTTCGGCCAAGGGACCAAGGTGGAAA<br>TCAAA |
| 26 | 4 | GAGGTGCAGCTGTTGGAGTCTGGGGGAGGCTTGGTACAGCCTGGGGGGTCCCTGAGACTCTCCT<br>GTGCAGCCTCTGGATTCACCTTTAGCAGCTATGCCATGAGCTGGGTCCGCCAGGCTCCAGGGAA<br>GGGGCTGGAGTGGGTCTCATCTATTTAGGGTCAGGGTCGGATTACACGGTACGCAGACTCCGTG<br>AAGGGCCGGTTCACCATCTCCAGAGACAATTCCAAGAACACGCTGTATCTGCAAATGAACAGCCT<br>GAGAGCCGAGGACACGGCCGTATATTACTGTGCGAAACGTGCGATTATGTTTGACTACTGGGGCC<br>AGGGAACCCTGGTCACCGTCTCGAGCGGTGGAGGCGGTTCAGGCGGAGGTGGCAGCGGCGGTG<br>GCGGGTCGACGGACATCCAGATGACCCAGTCTCCATCCTCCCTGTCTGCATCTGTAGGAGACAGA<br>GTCACCATCACTTGCCGGGCAAGTCAGAGCATTAGCAGCTATTTAAATTGGTATCAGCAGAAACCA<br>GGGAAAGCCCCTAAGCTCCTGATCTATCATGCATCCCTGTTGCAAAGTGGGGTCCCATCAAGGTT<br>CAGTGGCAGTGGATCTGGGACAGATTTCACTCTCACCATCAGCAGTCTGCAACCTGAAGATTTTGC<br>AACTTACTACTGTCAACAGGCTAGGTATTGGCCTCTGACGTTCGGCCAAGGGACCAAGGTGGAAA<br>TCAAA |

TABLE 2

| PROTEIN SEQUENCES FOR ScFv | | |
|---|---|---|
| Clone | SEQ ID NO: | Variable Sequence |
| 1 | 5 | EVQLLESGGGLVQPGGSLRLSCAASGFTFSSYAMSWVRQAPGKGLEWVSGIQSTGALTAYADSVKG<br>RFTISRDNSKNTLYLQMNSLRAEDTAVYYCAKLAQTFDYWGQGTLVTVSSGGGGSGGGGSGGGGST<br>DIQMTQSPSSLSASVGDRVTITCRASQSISSYLNWYQQKPGKAPKLLIYRASSLQSGVPSRFSGSGSG<br>TDFTLTISSLQPEDFATYYCQQTRRLPVTFGQGTKVEIK |
| 15 | 6 | EVQLLESGGGLVQPGGSLRLSCAASGFTFSSYAMSWVRQAPGKGLEWVSGISAQGAHTTYADSVKG<br>RFTISRDNSKNTLYLQMNSLRAEDTAVYYCAKTYKGFDYWGQGTLVTVSSGGGGSGGGGGGGGST<br>DIQMTQSPSSLSASVGDRVTITCRASQSISSYLNWYQQKPGKAPKLLIYSASRLQSGVPSRFSGSGSG<br>TDFTLTISSLQPEDFATYYCQQGRRMPPTFGQGTKVEIK<br>EVQLLESGGGLVQPGGSLRLSCAASGFTFSSYAMSWVRQAPGKGLEWVSGISAQGAHTTYADSVKG<br>RFTISRDNSKNTLYLQMNSLRAEDTAVYYCAKTYKGFDYWGQGTLVTVSSGGGGSGGGGSGGGGST<br>DIQMTQSPSSLSASVGDRVTITCRASQSISSYLNWYQQKPGKAPKLLIYSASRLQSGVPSRFSGSGSG<br>TDFTLTISSLQPEDFATYYCQQGRRMPPTFGQGTKVEIK |
| 19 | 7 | EVQLLESGGGLVQPGGSLRLSCAASGFTFSSYAMSWVRQAPGKGLEWVSAIASQGVATGYADSVKGR<br>FTISRDNSKNTLYLQMNSLRAEDTAVYYCAKLDQHFDYWGQGTLVTVSSGGGGSGGGGSGGGGSTDI<br>QMTQSPSSLSASVGDRVTITCRASQSISSYLNWYQQKPGKAPKLLIYQASRLQSGVPSRFSGSGSGTDF<br>TLTISSLQPEDFATYYCQQARRLPLTFGQGTKVEIK |
| 26 | 8 | EVQLLESGGGLVQPGGSLRLSCAASGFTFSSYAMSWVRQAPGKGLEWVSSIQGQGRITRYADSVKG<br>RFTISRDNSKNTLYLQMNSLRAEDTAVYYCAKRAIMFDYWGQGTLVTVSSGGGGSGGGGSGGGGST<br>DIQMTQSPSSLSASVGDRVTITCRASQSISSYLNWYQQKPGKAPKLLIYHASLLQSGVPSRFSGSGSGT<br>DFTLTISSLQPEDFATYYCQQARYWPLTFGQGTKVEIK |

TABLE 3

| CDR HEAVY CHAIN SEQUENCES | | | |
|---|---|---|---|
| Clone | CDRH1 (SEQ ID NO:) | CDRH2 (SEQ ID NO:) | CDRH3 (SEQ ID NO:) |
| scFv-1 | SYAMS (9) | GIQSTGALTAYADSVKGRFT (10) | LAQTFDY (11) |
| scFv-15 | SYAMS (9) | GISAQGAHTTYADSVKGRFT (12) | TYKGFDY (13) |
| scFv-19 | SYAMS (9) | AIASQGVATGYADSVKGRFT (14) | LDQHFDY (15) |
| scFv-26 | SYAMS (9) | SIQGQGRITRYADSVKGRFT (16) | RAIMFDY (17) |

TABLE 4

| CDR LIGHT CHAIN SEQUENCES | | | |
|---|---|---|---|
| Clone | CDRL1 (SEQ ID NO:) | CDRL2 (SEQ ID NO:) | CDRL3 (SEQ ID NO:) |
| scFv-1 | ISSYLN (18) | IYRASSLQS (19) | QQTRRLPVT (20) |
| scFv-15 | ISSYLN (18) | IYSASRLQS (21) | QQGRRMPPT (22) |
| scFv-19 | ISSYLN (18) | IYQASRLQS (23) | QQARRLPLT (24) |
| scFv-26 | ISSYLN (18) | IYHASLLQS (25) | QQARYWPLT (26) |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VIII. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
U.S. Pat. No. 6,485,982
"Antibodies: A Laboratory Manual," Cold Spring Harbor Press, Cold Spring Harbor, NY, 1988.
Abbondanzo et al., *Am. J. Pediatr. Hematol. Oncol.* 12(4): 480-489, 1990.
Allred et al., *Arch. Surg.* 125(1), 107-113:1990.
Atherton et al., *Biol. of Reproduction* 32:155-171, 1985.
Beltramello et al., *Cell Host Microbe* 8:271-283, 2010.
Brown et al., *J. Immunol. Meth.* 130(1): 111-121, 1990.
Campbell, *In: Monoclonal Antibody Technology, Laboratory Techniques in Biochemistry and Molecular Biology*, Vol. 13, Burden and Von Knippenberg, Eds. pp. 75-83, Amsterdam, Elsevier, 1984.
Capaldi et al., *Biochem. Biophys. Res. Comm.* 74(2):4 25-433, 1977.
De Jager et al., *Semin. Nucl. Med.* 23(2): 165-179, 1993.
Dholakia et al., *J. Biol. Chem.* 264: 20638-20642, 1989.
Doolittle and Ben-Zeev, *Methods Mol. Biol.* 109: 215-237, 1999.
Gefter et al., *Somatic Cell Genet.* 3:231-236, 1977.
Gulbis and Galand, *Hum. Pathol.* 24(12): 1271-1285, 1993.
Hessell et al., *Nature* 449: 101-104, 2007.
Khatoon et al., *Ann. of Neurology* 26: 210-219, 1989.
King et al., *J. Biol. Chem.* 269: 10210-10218, 1989.
Kohler and Milstein, *Eur. J. Immunol.* 6: 511-519, 1976.
Kohler and Milstein, *Nature* 256: 495-497, 1975.
Kyte and Doolittle, *J. Mol. Biol.* 157(1): 105-132, 1982.
Nakamura et al., *In: Enzyme Immunoassays: Heterogeneous and Homogeneous Systems, Chapter* 27, 1987.
O'Shannessy et al., *J. Immun. Meth.* 99: 153-161, 1987.
Persic et al., *Gene* 187: 1, 1997
Potter and Haley, *Meth. Enzymol.* 91: 613-633, 1983.
Remington's Pharmaceutical Sciences, 15th Ed., 3:624-652, 1990.
Tang et al., *J. Biol. Chem.,* 271: 28324-28330, 1996.
Wawrzynczak & Thorpe, In: *Immunoconjugates, Antibody Conuugates In Radioimaging And Therapy Of Cancer*, Vogel (Ed.), NY, Oxford University Press, 28, 1987.

Yu et al., *J Immunol Methods* 336: 142-151, 2008.
Siegel, R. L., Miller, K. D. & Jemal, A. *CA Cancer J Clin* 69, 7-34, doi:10.3322/caac.21551 (2019).
Rahib, L. et al., *Cancer Res* 74, 2913-2921, doi:10.1158/0008-5472.CAN-14-0155 (2014).
Oettle, H. et al., *JAMA* 310, 1473-1481, doi:10.1001/jama.2013.279201 (2013).
Oettle, H. et al. Adjuvant chemotherapy with gemcitabine vs observation in patients undergoing curative-intent resection of pancreatic cancer: a randomized controlled trial. *JAMA* 297, 267-277, doi:10.1001/jama.297.3.267 (2007).
Conroy, T. et al., *N Engl J Med* 364, 1817-1825, doi:10.1056/NEJMoa1011923 (2011).
Conroy, T. et al., *N Engl J Med* 379, 2395-2406, doi:10.1056/NEJMoa1809775 (2018).
Siegel, R., Ma, J., Zou, Z. & Jemal, A., *CA Cancer J Clin* 64, 9-29, doi:10.3322/caac.21208 (2014).
Sinn, M. et al., *J Clin Oncol* 35, 3330-3337, doi:10.1200/JCO.2017.72.6463 (2017).
Moore, M. J. et al., *J Clin Oncol* 25, 1960-1966, doi:10.1200/JCO.2006.07.9525 (2007).
Manji, G. A., Olive, K. P., Saenger, Y. M. & Oberstein, P. Current and Emerging Therapies in Metastatic Pancreatic Cancer. *Clin Cancer Res* 23, 1670-1678, doi:10.1158/1078-0432.CCR-16-2319 (2017).
Von Hoff, D. D. et al., *N Engl J Med* 369, 1691-1703, doi:10.1056/NEJMoa1304369 (2013).
Le, D. T. et al., *Science* 357, 409-413, doi:10.1126/science.aan6733 (2017).
Boyiadzis, M. M. et al., *J Immunother Cancer* 6, 35, doi:10.1186/s40425-018-0342-x (2018).
Hu, Z. I. et al., *Clin Cancer Res* 24, 1326-1336, doi:10.1158/1078-0432.CCR-17-3099 (2018).
Ott, P. A. et al., *J Clin Oncol* 37, 318-327, doi:10.1200/JCO.2018.78.2276 (2019).
Brahmer, J. R. et al., *N Engl J Med* 366, 2455-2465, doi:10.1056/NEJMoa1200694 (2012).
Clark, C. E. et al., *Cancer Res* 67, 9518-9527, doi:10.1158/0008-5472.CAN-07-0175 (2007).
Hiraoka, N., Onozato, K., Kosuge, T. & Hirohashi, S., *Clin Cancer Res* 12, 5423-5434, doi:10.1158/1078-0432.CCR-06-0369 (2006).
Hu, H. et al., *Tumour Biol* 37, 8657-8664, doi:10.1007/s13277-015-4741-z (2016).
Sive, H. L., Hattori, K. & Weintraub, H., *Cell* 58, 171-180, doi:10.1016/0092-8674 (89) 90413-3 (1989).
Aberger, F., Weidinger, G., Grunz, H. & Richter, K., *Mech Dev* 72, 115-130, doi:10.1016/s0925-4773 (98) 00021-5 (1998).
Riener, M. O. et al., *Histol Histopathol* 24, 1121-1128, doi:10.14670/HH-24.1121 (2009).
Dumartin, L. et al., *Cancer Res* 71, 7091-7102, doi:10.1158/0008-5472.CAN-11-1367 (2011).
Chen, R. et al., *Mol Cancer* 9, 149, doi:10.1186/1476-4598-9-149 (2010).
Le Large, T. Y. S. et al., *Semin Cancer Biol* 44, 153-169, doi:10.1016/j.semcancer.2017.03.008 (2017).
Ramachandran, V., Arumugam, T., Wang, H. & Logsdon, C. D., *Cancer Res* 68, 7811-7818, doi:10.1158/0008-5472.CAN-08-1320 (2008).
Dumartin, L. et al., *Oncogene* 36, 3094-3103, doi:10.1038/one.2016.459 (2017).
Di Maro, G. et al., *Mol Cancer* 13, 160, doi:10.1186/1476-4598-13-160 (2014).
Ma, S. R. et al., *Am J Transl Res* 9, 507-519 (2017).
Wang, Z., Hao, Y. & Lowe, A. W., *Cancer Res* 68, 492-497, doi:10.1158/0008-5472.CAN-07-2930 (2008).
Boj, S. F. et al., *Cell* 160, 324-338, doi:10.1016/j.cell.2014.12.021 (2015).
Norris, A. M. et al., *Oncogene* 32, 3867-3876, doi:10.1038/one.2012.394 (2013).
Singh, P., Srinivasan, R. & Wig, J. D., *Pancreas* 41, 541-546, doi:10.1097/MPA.0b013e318247d6af (2012).

What is claimed is:

1. A method of detecting an AGR2-expression or overexpressing cancer in a subject comprising:

(a) contacting a sample from said subject with an antibody, single chain antibody or antibody fragment comprising heavy chain CDRl-3 comprising SEQ ID NOS: 9-11, respectively, and light chain CDRl-3 comprising SEQ ID NOS: 18-20, respectively, or comprising heavy chain CDRl-3 comprising SEQ ID NOS: 9, 12 and 13, respectively, and light chain CDRl-3 comprising SEO ID NOS: 18, 21 and 22, respectively, or comprising heavy chain CDRl-3 SEQ ID NOS: 9, 14 and 15, respectively, and light chain CDRl-3 comprising SEQ ID NOS: 18, 23 and 24, respectively, or comprising heavy chain CDRl-3 SEQ ID NOS: 9, 16 and 17, respectively, and light chain CDRl-3 comprising SEQ ID NOS: 18, 25 and 26, respectively; and (b) detecting an AGR2-expression or overexpressing cancer cells in said sample by binding of said antibody, single chain antibody or antibody fragment to a cancer cell in said sample.

2. A method of treating a subject having an AGR2-expressing or overexpressing cancer comprising delivering to said subject an antibody, single chain antibody or antibody fragment comprising heavy chain CDRl-3 comprising SEQ ID NOS: 9-11, respectively, and light chain CDRl-3 comprising SEQ ID NOS: 18-20, respectively, or comprising heavy chain CDRl-3 comprising SEQ ID NOS: 9, 12 and 13, respectively, and light chain CDRl-3 comprising SEO ID NOS: 18, 21 and 22, respectively, or comprising heavy chain CDRl-3 SEQ ID NOS: 9, 14 and 15, respectively, and light chain CDRl-3 comprising SEQ ID NOS: 18, 23 and 24, respectively, or comprising heavy chain CDRl-3 SEQ ID NOS: 9, 16 and 17, respectively, and light chain CDRl-3 comprising SEQ ID NOS: 18, 25 and 26, respectively; and (b) detecting an AGR2-expression or overexpressing cancer cells in said sample by binding of said antibody, single chain antibody or antibody fragment to a cancer cell in said sample.

3. The method of claim 2, wherein said antibody, single chain antibody or antibody fragment comprises SEQ ID NO: 5, SEQ ID NO: 6, SEQ ID NO: 7, or SEQ ID NO: 8.

4. The method of claim 2, wherein the antibody fragment is a Fab fragment, $F(ab')_2$ fragment, or Fv fragment.

5. The method of claim 2, wherein said antibody is an IgG, or a recombinant IgG antibody or antibody fragment comprising an Fc portion mutated to (eliminate or enhance FcR interactions, to increase half-life and/or increase therapeutic efficacy, or glycan modified to eliminate or enhance FcR interactions.

6. The method of claim 5, wherein said recombinant IgG antibody or antibody fragment mutated to eliminate or enhance FcR interactions, to increase half-life and/or increase therapeutic efficacy comprises a LALA, LALA-PG, N297, GASD/ALIE, DHS, YTE or LS mutation or is glycan modified by enzymatic or chemical addition or removal of glycans or expression in a cell line engineered with a defined glycosylating pattern.

7. The method of claim 2, wherein said antibody is a chimeric antibody or a bispecific antibody.

8. The method of claim 7, wherein said bispecific antibody is a bispecific T-cell engager.

9. The method of claim 8, wherein said bispecific T-cell engager comprises an Fc portion mutated to eliminate or enhance FcR interactions, to increase half-life and/or increase therapeutic efficacy, or glycan modified to eliminate or enhance FcR interactions.

10. The method of claim 9, wherein said bispecific T-cell engager mutated to eliminate or enhance FcR interactions, to increase half-life and/or increase therapeutic efficacy comprises a LALA, LALA-PG, N297, GASD/ALIE, DHS, YTE or LS mutation or is glycan modified to eliminate or enhance FcR interactions by enzymatic or chemical addition or removal of glycans or expression in a cell line engineered with a defined glycosylating pattern.

11. An antibody, single chain antibody or antibody fragment, comprising heavy chain CDRl-3 comprising SEQ ID NOS: 9-11, respectively, and light chain CDRl-3 comprising SEQ ID NOS: 18-20, respectively, or comprising heavy chain CDRl-3 comprising SEQ ID NOS: 9, 12 and 13, respectively, and light chain CDRl-3 comprising SEO ID NOS: 18, 21 and 22, respectively, or comprising heavy chain CDRl-3 SEQ ID NOS: 9, 14 and 15, respectively, and light chain CDRl-3 comprising SEQ ID NOS: 18, 23 and 24, respectively, or comprising heavy chain CDRl-3 SEQ ID NOS: 9, 16 and 17, respectively, and light chain CDRl-3 comprising SEQ ID NOS: 18, 25 and 26, respectively.

12. The antibody, single chain antibody or antibody fragment of claim 11 is encoded by SEQ ID NO: 1, SEQ ID NO: 2, SEQ ID NO: 3, or SEQ ID NO: 4.

13. The antibody, single chain antibody or antibody fragment of claim 11 is encoded by a sequence having at least 70%, 80%, 90%, or 95% identity to SEQ ID NO: 1, SEQ ID NO: 2, SEQ ID NO: 3, or SEQ ID NO: 4.

14. The antibody, single chain antibody or antibody fragment of claim 11 comprises SEQ ID NO: 5, SEQ ID NO: 6, SEQ ID NO: 7, or SEQ ID NO: 8.

15. The antibody, single chain antibody or antibody fragment of claim 11 comprises a sequence having 70%, 80%, 90%, or 95% identity to SEQ ID NO: 5, SEQ ID NO: 6, SEQ ID NO: 7, or SEQ ID NO: 8.

16. The antibody, single chain antibody or antibody fragment of claim 11, wherein the antibody fragment is Fab fragment, $F(ab')_2$ fragment, or Fv fragment.

17. The antibody, single chain antibody or antibody fragment of claim 11, wherein said antibody is a chimeric antibody, or is bispecific antibody.

18. The monoclonal antibody of claim 17, wherein said bispecific antibody is a Bi-specific T-cell engager, comprising an Fc portion mutated to eliminate or enhance FcR interactions, to increase half-life and/or increase therapeutic efficacy, or glycan modified to eliminate or enhance FcR interactions.

19. The method of claim 18, wherein said bispecific T-cell engager mutated to eliminate or enhance FcR interactions, to increase half-life and/or increase therapeutic efficacy comprises a LALA, LALA-PG, N297, GASD/ALIE, DHS, YTE or LS mutation or is glycan modified to eliminate or enhance FcR interactions by enzymatic or chemical addition or removal of glycans or expression in a cell line engineered with a defined glycosylating pattern.

20. The antibody, single chain antibody or antibody fragment of claim 11, wherein said antibody is an IgG, or a recombinant IgG antibody or antibody fragment comprising an Fc portion mutated to alter (eliminate or enhance) FcR interactions, to increase half-life and/or increase therapeutic efficiency, comprising a LALA, LALA-PG, N297, GASD/ALIE, DHS, YTE, or LS mutation or glycan modified to eliminate or enhance FcR interactions comprising enzymatic or chemical addition or removal of glycans or expression in a cell line engineered with a defined glycosylating pattern.

21. The monoclonal antibody of claim 20, wherein said recombinant IgG antibody or antibody fragment mutated to eliminate or enhance FcR interactions, to increase half-life and/or increase therapeutic efficacy comprises a LALA, LALA-PG, N297, GASD/ALIE, DHS, YTE or LS mutation or is glycan modified by enzymatic or chemical addition or removal of glycans or expression in a cell line engineered with a defined glycosylating pattern.

22. A hybridoma or engineered cell encoding an antibody, single chain antibody or antibody fragment wherein the antibody, single chain antibody or antibody fragment comprising heavy chain CDRl-3 comprising SEQ ID NOS: 9-11, respectively, and light chain CDRl-3 comprising SEQ ID NOS: 18-20, respectively, or comprising heavy chain CDRl-3 comprising SEQ ID NOS: 9, 12 and 13, respectively, and light chain CDRl-3 comprising SEO ID NOS: 18, 21 and 22, respectively, or comprising heavy chain CDRl-3 SEQ ID NOS: 9, 14 and 15, respectively, and light chain CDRl-3 comprising SEQ ID NOS: 18, 23 and 24, respectively, or comprising heavy chain CDRl-3 SEQ ID NOS: 9, 16 and 17, respectively, and light chain CDRl-3 comprising SEQ ID NOS: 18, 25 and 26, respectively; and (b) detecting an AGR2-expression or overexpressing cancer cells in said sample by binding of said antibody, single chain antibody or antibody fragment to a cancer cell in said sample.

23. The hybridoma or engineered cell encoding an antibody of claim 22, wherein said antibody, single chain antibody or antibody fragment comprises SEQ ID NO: 5, SEQ ID NO: 6, SEQ ID NO: 7, or SEQ ID NO: 8.

24. A chimeric antigen receptor comprising:

(i) an ectodomain comprising single chain antibody variable region comprising heavy chain CDRl-3 comprising SEQ ID NOS: 9-11, respectively, and light chain CDRl-3 comprising SEQ ID NOS: 18-20, respectively, or comprising heavy chain CDRl-3 comprising SEQ ID NOS: 9, 12 and 13, respectively, and light chain CDRl-3 comprising SEO ID NOS: 18, 21 and 22, respectively, or comprising heavy chain CDRl-3 SEQ ID NOS: 9, 14 and 15, respectively, and light chain CDRl-3 comprising SEQ ID NOS: 18, 23 and 24, respectively, or comprising heavy chain CDRl-3 SEQ ID NOS: 9, 16 and 17, respectively, and light chain CDRl-3 comprising SEQ ID NOS: 18, 25 and 26, respectively; and with a flexible hinge attached at the C-terminus of said single chain antibody variable region;

(ii) a transmembrane domain; and (iii) an endodomain, wherein said endodomain comprises a signal transduction function when said single-chain antibody variable region is engaged with MUC1.

25. The chimeric antigen receptor of claim 24, wherein said antibody, single chain antibody or antibody fragment comprises SEQ ID NO: 5, SEQ ID NO: 6, SEQ ID NO: 7, or SEQ ID NO: 8.

* * * * *